United States Patent [19]

Kadin

[11] 4,414,388
[45] Nov. 8, 1983

[54] 1-OXO-1H-THIAZOLO[3,2-A]PYRIMIDINE-2-CARBOXAMIDES

[75] Inventor: Saul B. Kadin, New London, Conn.

[73] Assignee: Pfizer Inc., New York, N.Y.

[21] Appl. No.: 330,578

[22] Filed: Dec. 14, 1981

Related U.S. Application Data

[63] Continuation of Ser. No. 96,631, Nov. 23, 1979, abandoned.

[51] Int. Cl.³ ............... C07D 513/02; A61K 31/505
[52] U.S. Cl. ............................... 544/48; 424/251
[58] Field of Search ........................... 544/48

[56] References Cited

U.S. PATENT DOCUMENTS

| | | | |
|---|---|---|---|
| 3,887,574 | 6/1975 | Ellis et al. | 548/251 |
| 4,041,163 | 3/1976 | Bindva et al. | 424/251 |
| 4,223,031 | 9/1980 | Covington et al. | 544/48 |

Primary Examiner—Donald G. Daus
Assistant Examiner—D. B. Springer
Attorney, Agent, or Firm—Connolly and Hutz

[57] ABSTRACT

Antiallergy and antiulcer agents having the formula (I),

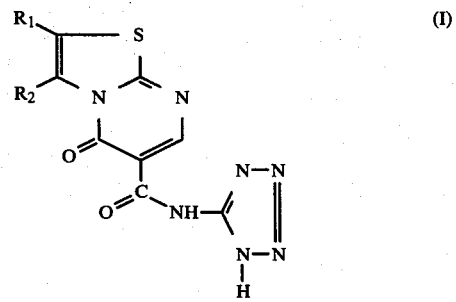

and their pharmaceutically acceptable salts, wherein $R_1$ and $R_2$ taken separately are each hydrogen or lower alkyl; and $R_1$ and $R_2$ taken together are alkylene of 3–9 carbon atoms or phenylalkylene of 9–11 carbon atoms, with the proviso that the ring so formed is between 5- and 8-membered; acids of the formula (II),

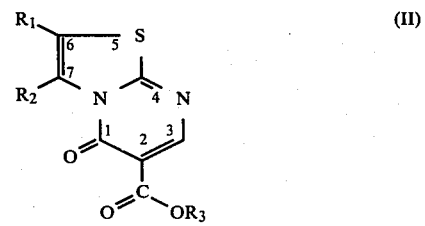

wherein $R_1$ and $R_2$ are as defined above and $R_3$ is hydrogen, which are useful as intermediates for compounds of the formula (I), but in many instances also possess the same useful biological activity as do formula I compounds; and intermediates of the formula II wherein $R_1$ and $R_2$ are defined as above, and $R_3$ is alkyl of 1 to 4 carbon atoms, carbalkoxy of 2 to 5 carbon atoms, carbophenoxy or carbobenzoxy, are also described.

9 Claims, No Drawings

1-OXO-1H-THIAZOLO[3,2-A]PYRIMIDINE-2-CARBOXAMIDES

This application is a continuation of application Ser. No. 96,631 filed Nov. 23, 1979 and now abandoned.

BACKGROUND OF THE INVENTION

This invention relates to novel derivatives of 1-oxo-1H-thiazolo[3,2-a]pyrimidine-2-carboxamides and their acid precursors. These amides, and in many cases their acid precursors, are useful in preventing release of allergic mediators (histamine, serotonin, SRS-A, etc.) and may be used, therefore, to treat bronchial asthma, hay fever, rhinitis, atopic dermatitis, etc., and further, are useful as antiulcer agents.

Allergic reactions, the symptoms resulting from an antigen-antibody interaction, manifest themselves in a wide variety of ways and in different organs and tissues. Common allergic disorders, for example, are allergic rhinitis, a condition characterized by seasonal or perennial sneezing, running nose, nasal congestion, with itching and congestion of eyes; hay fever, a variety of allergic rhinitis that results from hypersensitivity to grass pollens; and bronchial asthma, one of the most disabling and debilitating of allergic reactions, a disease characterized by hyper-reactivity of the bronchi on exposure to various immunogenic or nonimmunogenic stimuli, resulting in bronchospasms with wheezing, short-lived paroxysms and widespread constriction of airway passages. The mechanical obstruction to airflow in airways is generally reversed by the use of bronchodilators, which provide symptomatic relief. In contrast, antiallergy agents prevent the release of mediators of anaphylaxis from tissue stores, thereby acting in a prophylactic manner to preclude elicitation of broncho-constriction by the mediators.

Cox and co-workers, Adv. in Drug Res., 5, 115 (1970), described the pharmacology of disodium cromoglycate [1,3-bis(2-carboxycromon-5-yloxy)-2-hydroxy-propane, Intal]. It is not a bronchodilator, but mediates its therapeutic effects by inhibition of release of mediators of anaphylaxis and is administered prophylactically. It suffers from lack of oral efficacy and, for optimum results, is administered by inhalation as a solid inhalant.

More recently, a variety of other antiallergy agents have been described, including N-(5-tetrazolyl)-1-oxo-1H-6-alkoxypyrimido-[1,2-a]quinoline-2-carboxamides (Kadin, U.S. Pat. No. 4,017,625), 1-oxo-1H-6-substituted-pyrimido[1,2-a]quinoline-2-carboxylic acids (Kadin, U.S. Pat. No. 4,066,766), tetrazolo[a]quinazol-5-ones (Bindra, U.S. Pat. No. 4,085,213), pyrimido[2,1-a]isoquinolines (Jubyet al., U.S. Pat. No. 4,127,720), and N-(5-tetrazoyl)-4-oxo-4H-pyrimido(2,1-b)benzothiazole-3-carboxamides (Bindra and Kadin, U.S. Pat. No. 4,041,163).

Chronic gastric and duodenal ulcers, collectively known as peptic ulcers, are a common affliction for which a variety of treatments have been developed. The treatment depends upon the severity of the ulcer and may range from dietary and medical (drug) treatment to surgery. A wide variety of drugs have been used to treat ulcers; the most recent of which to gain widespread attention is carbenoxolone sodium, the disodium salt of the hemisuccinate of glycyrrhetinic acid. It is reported to prevent formation of and to accelerate healing of gastric ulcers in animals, including humans ("Carbenoxolone Sodium: A Symposium," J. M. Robson and F. M. Sullivan, Eds., Butterworths, London, 1968). However, its use is accompanied by undesirable aldosterone-like side effects, such as marked antidiuretic and sodium-retaining activity and, oftentimes, potassium loss, such that continued therapy with this agent often leads to hypertension, muscle weakness and, ultimately, congestive heart failure. More recently, a histamine receptor antagonist, cimetidine, has been introduced into medical practice. The latter compound alleviates ulcers by reducing gastric acid secretion.

A variety of other compounds have been reported to possess antiulcer activity, including 1-oxo-1H-6-piperidinopyrimidino[1,2-a]quinoline-2-carboxylic esters (Kadin and Moore, U.S. Pat. No. 4,014,881), 1-oxo-1H-6-substituted-pyrimido(1,2-a)quinoline-2-carboxylic acids and esters (Kadin and Moore, U.S. Pat. No. 4,031,217), tetrazolo[a]quinazol-5-ones (Bindra, U.S. Pat. No. 4,085,213).

The amides and most of the intermediate acids of the present invention are novel compounds. The known acids are those of formula II wherein $R_1$ and $R_2$ are hydrogen or $R_1$ is methyl and $R_2$ is hydrogen [Dunwell et al., J. Chem. Soc. (C), 1971, 2094]. The corresponding ethyl esters are also known, together with the ethyl ester in which $R_1$ is methyl and $R_2$ is hydrogen [Dunwell et al., J. Chem. Soc. (C) 1971, 2094; Allen et al., J. Org. Chem. 24, 779 (1959)]. Neither of these publications disclose a utility for either the acids or the esters.

SUMMARY OF THE INVENTION

It has now been found that compounds having the formula (I)

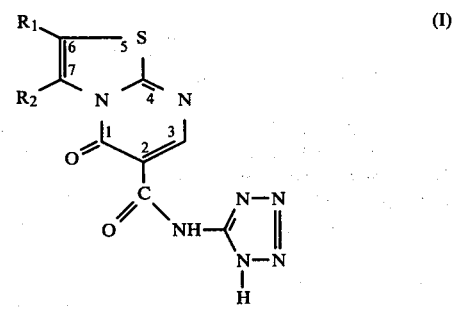

and their pharmaceutically acceptable cationic salts are orally effective antiallergy and antiulcer agents. In the formula (I), $R_1$ and $R_2$ are each hydrogen or lower alkyl of 1 to 5 carbon atoms [such as methyl, ethyl, propyl, isopropyl, 2-methyl-2-propyl(tert.-butyl), 2-butyl, 2-methyl-1-propyl(isobutyl), pentyl, etc.] or $R_1$ and $R_2$ taken together, forming a third, 5- to 8-membered ring system, are alkylene of 3 to 9 carbon atoms, e.g.:

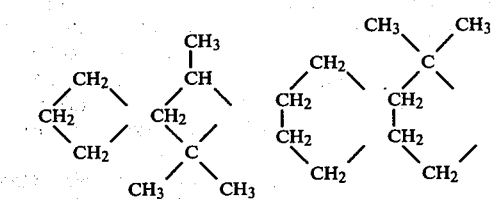

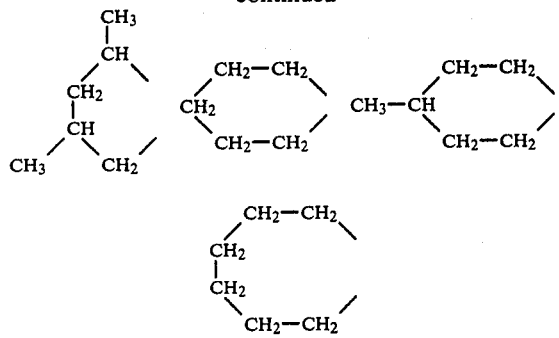

or phenyl alkylene of 9–11 carbon atoms, e.g.:

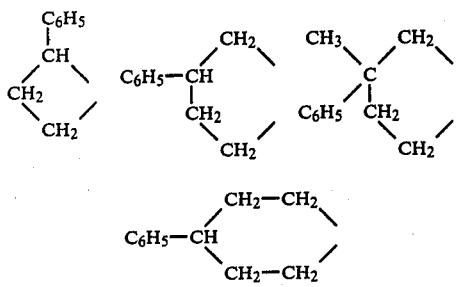

It has also been found that acids of the formula (II),

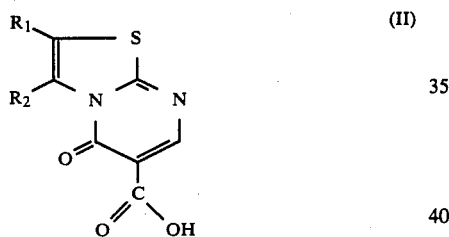

wherein $R_1$ and $R_2$ are as defined above, are not only valuable intermediates for the synthesis of the amides, but in many instances, together with their pharmaceutically-acceptable cationic salts, also have useful biological activity. Acids possessing useful antiallergy activity are those wherein $R_1$ and $R_2$ when taken together are alkylene of 4 to 9 carbon atoms or phenylalkylene of 9 to 11 carbon atoms, with the proviso that the ring system so formed is 5- to 8-membered, or, when taken separately, $R_1$ is alkyl of 2 to 5 carbon atoms and $R_2$ is hydrogen or alkyl of 1 to 5 carbon atoms. The preferred acids for antiallergy use are those wherein $R_1$ and $R_2$ are taken together and are alkylene of 4 to 6 carbon atoms, particularly butylene. Acids of somewhat different structure possess usseful antiulcer activity, viz., those wherein $R_1$ and $R_2$ when taken together are alkylene of 3 to 9 carbon atoms or phenylalkylene of 9 to 11 carbon atoms, with the proviso that the ring system so formed is 5- to 8-membered, or $R_1$ and $R_2$ when taken separately are each hydrogen or alkyl of 1 to 5 carbon atoms, with the proviso that when $R_2$ is hydrogen, $R_1$ is other than hydrogen or methyl. In this case the preferred compounds are those wherein $R_1$ and $R_2$ are taken separately, particularly when $R_1$ is ethyl and $R_2$ is hydrogen or alkyl of 1 to 2 carbon atoms.

By the term "pharmaceutically-acceptable cationic salts" is intended salts such as the alkali metal salts, e.g., sodium and potassium; alkaline earth metal salts such as calcium and magnesium; aluminum salts; ammonium salts; and salts with organic bases, e.g., amines such as triethylamine, tributylamine, piperidine, triethanolamine, diethylaminoethylamine, N,N'-dibenzylethylenediamine and pyrrolidine.

The 5-substituted tetrazoles, as is known, can exist in two isomeric forms, viz:

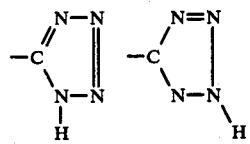

which co-exist in a dynamic tautomeric, equilibrium mixture. Both forms of the tetrazolyl amides are included within the scope of this invention.

The compounds of particular interest in this invention are those of the formula (I) in which $R_1$ is hydrogen or methyl and $R_2$ is methyl. Of these, the compound in which $R_1$ is hydrogen is preferred, since the corresponding acid, believed to be its metabolite, also shows activity. Also of particular interest are those compounds in which $R_1$ and $R_2$ taken together are propylene, butylene, or pentylene. Especially desirable is the compound in which $R_1$ and $R_2$ together are butylene, i.e., N-(5-tetrazolyl)-1-oxo-1H-cyclohexenothiazolo-[3,2-a]pyrimidine-2-carboxamide (formula III)

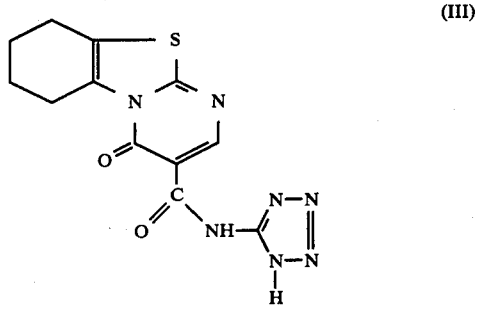

since it shows excellent oral activity and is highly stable in a pure solid state, as well as in the presence of standard pharmaceutical diluents and in solution. Furthermore, its metabolite (the corresponding carboxylic acid) shows good activity. The preferred form of the tetrazolyl amide (III) is the sodium salt (trihydrate), which is non-hygroscopic and has good water solubility, ensuring good bioavailability.

The antiallergy property of the compounds of this invention is evaluated by the passive cutaneous anaphylaxis (PCA) test (Ovary, J. Immun., 81, 355, 1958). In the PCA test, normal animals are injected intradermally (i.d.) with antibodies contained in serum obtained from actively sensitized animals. The animals are then challenged intravenously with antigen mixed with a dye such as Evans' Blue. The increased capillary permeability caused by the antigen-antibody reaction causes the dye to leak from the site of the antibody injection. The test animals are then asphyxiated and the intensity of the reaction determined by measuring the diameter and intensity of the blue coloration on the inner surface of the animals' skin.

The antiulcer activity of the compounds of the present invention is evaluated by the so-called cold-restraint stressed rat assay. Alternatively, the antiulcer activity is determined in a newly established ethanol-induced rat ulcer assay described below.

Detailed Description of the Invention

The compounds of this invention are prepared by the following routes:

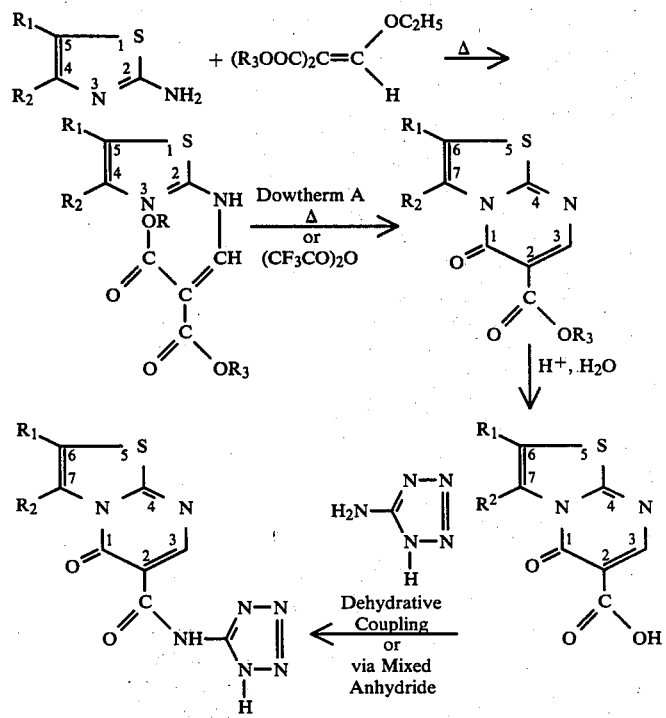

In the first stage of the synthetic sequence, the appropriately substituted 2-aminothiazole is condensed with a stoichiometric amount of a dialkyl ethoxymethylenemalonate, usually with the readily available diethyl ethoxymethylenemalonate, the choice of ester not being critical to obtaining the ultimately desired products of this invention. The condensation is carried out at a temperature of from about 80° C. to about 125° C. Lower temperatures are not desirable because the reaction proceeds at too slow a rate. Higher temperatures can be used but appear to offer no advantages. The reaction is thus conveniently carried out as a melt. It can, of course, be conducted in a solvent or mixture of solvents; for example, ethanol, N,N-dimethylformamide, acetonitrile. However, from a practical standpoint, a solvent appears unnecessary. The products of this condensation are 4- and/or 5-substituted-2-(2,2-dicarbalkoxyethenylamino)thiazoles. It will be noted that when $R_1$ and $R_2$ taken together form a ring system, the nomenclature and numbering systems are modified as follows:

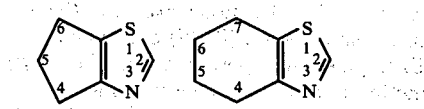

Cyclopentenothiazole   Cyclohexeneothiazole

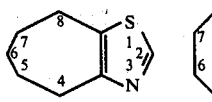 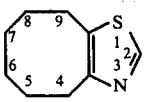

Cycloheptenothiazole   Cyclooctenothiazole

An alternative nomenclature for the cyclohexeno- thiazoles is tetrahydrobenzothiazoles.

The second stage of the synthetic sequence is cyclization of the 4- and/or 5-substituted 2-(2,2-dicarbalkoxyethenylaminothiazoles with elimination of one equivalent of alkanol (ethanol in the case of the ethyl ester). By one method, this cyclization is accomplished by heating the intermediate to a temperature of from about 175° C., to about 250° C. until reaction is essentially complete, usually in about one to two hours. The cyclization is advantageously achieved by heating the intermediate in a suitable reaction-inert diluent; that is, in a compound which permits control of the reaction temperature, is stable to the relatively high temperatures employed and which does not react with the starting material or the products of cyclization. Representative of such diluents are high boiling hydrocarbons such as perhydronaphthalene, mineral oil, diethylbenzene, acetic anhydride containing sulfuric acid, diphenyl ether and diphenyl, especially that which contains 26.5% diphenyl and 73.5% diphenyl ether and is sold under the trademark Dowtherm A.

The cyclization is alternatively carried out under milder conditions (70°–130° C.) by heating the intermediate in the presence of an excess (1.1 to 3 equivalents) of trifluoroacetic anhydride in an inert solvent such as toluene, until reaction is complete (e.g. 15–20 hours at the reflux temperature of toluene). By either method, the products of the cyclization step are alkyl 1-oxo-1H-6-and/or-7-substituted-thiazolo[3,2-a]pyrimidine-2-carboxylates. It will be noted that when $R_1$ and $R_2$ taken together form a ring system, the nomenclature and numbering systems are modified as follows:

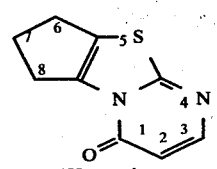

1-oxo-1H—cyclopenteno-
thiazolo[3,2-a]pyrimidine

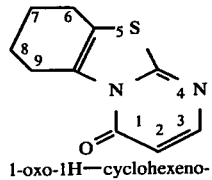

1-oxo-1H—cyclohexeno-
thiazolo[3,2-a]pyrimidine

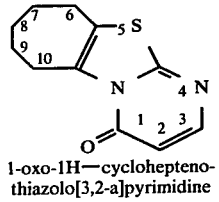

1-oxo-1H—cyclohepteno-
thiazolo[3,2-a]pyrimidine

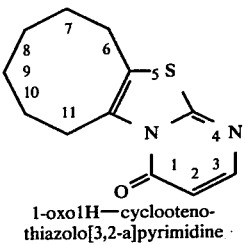

1-oxo1H—cyclooteno-
thiazolo[3,2-a]pyrimidine

The 1-oxo-1H-cyclohexenothiazolo[3,2-a]pyrimidines are alternatively named as 6,7,8,9-tetrahydro-1-oxo-1H-pyrimidino[2,1-b]benzthiazoles, or, using an alternative numbering system, 5,6,7,8-tetrahydro-4-oxo-4H-pyrimido (2,1-b)benthiazoles.

It is evident that the condensation and cyclization steps can be conducted in a single operation, without the need for separating the intermediate 2-(2,2-carbalkoxyethenylamino)thiazole, either by employing a sufficiently high reaction temperature so that both condensation and cyclization are effected, or by condensing as described above, followed by the addition of an inert solvent (if not already present) and an excess of trifluoracetic anhydride (2.1 to 4 equivalents) and proceeding with the cyclization step.

The favored procedure comprises separate steps of condensation and cyclization described above. Isolation of the intermediate compound and subsequent purification thereof before cyclization generally afford a better quality cyclized product.

The esters obtained by the above condensation/cyclization are then hydrolyzed to the corresponding 1-oxo-1H-6- and/or 7-substituted-thiazolo[3,2-a]pyrimidine-2-carboxylic acids. (Note the nomenclature and modified numbering systems described above when $R_1$ and $R_2$ taken together form a third ring.) Acid catalyzed hydrolysis is preferred. Refluxing the ester in 48% hydrobromic acid until hydrolysis is complete (0.5 to 3 hours is generally satisfactory) is a particularly suitable method. If foaming presents a problem, the hydrolysis can be carried out at slightly elevated pressure, e.g. 7 p.s.i.g. at 85° C.

The N-(5-tetrazolyl)amides of this invention are conveniently prepared by dehydrative coupling of the acids with 5-aminotetrazole. The dehydrative coupling is accomplished by means of a wide variety of agents commonly used in peptide syntheses. Representative agents include N,N'-carbonyldiimidazole, N,N'-carbonyl-di-s-triazine, ethoxyacetylene, 1,1-dichlorodiethylether, diphenylketene p-tolylimine, N-hydroxyphthalimide, N-hydroxysuccinimide, N-hydroxypiperidine, ethylene chlorophosphite, diethyl ethylene pyrophosphite, N-ethyl-5-phenylisoxazolium-3'-sulfonate, phenylphosphorodi-(1-imidazolate) and carbodiimides such as dicyclohexylcarbodimide, 1-cyclohexyl-3-(2-morpholinomethyl)carbodiimide, N-(3-dimethylaminopropyl[-N'-ethylcarbodiimide hydrochloride, 1-ethyl-3-(3'-dimethylaminopropyl]carbodiimide hydrochloride and diethyl cyanamide.

The above-described coupling agents are generally reacted first with the acid reactant and the resulting product then reacted without isolation with 5-aminotetrazole to afford the desired 1-oxo-1H-6- and/or 7-substituted-thiazolo[3,2-a]pyrimidine. (Note the nomenclature and modified numbering systems described above when $R_1$ and $R_2$ taken together form a third ring).

The reaction is carried out in a reaction-inert solvent system in which the acid reactant need not be soluble. The only requirement for the solvent system is that it not enter into any appreciable reaction with the reactants or products. The variety of coupling agents which can be used to bring about the dehydrative coupling allow a wide choice of solvents. Representative solvents are N,N-dimethylformamide, tetrahydrofuran, dioxane, methylene chloride, nitromethane and acetonitrile.

The reaction of the acid reactant with the coupling agent is conducted at a temperature of from about 20° C. to about 110° C. The reactive intermediate is then reacted with 5-aminotetrazole at from about 20° C. to 110° C. Each of these steps is advantageously carried out at from about 50° C. to about 100° C. since the rate and yield of the reaction are improved.

The molar ratio of acid:coupling agent:5-aminotetrazole is generally about 1:1:1 to about 1:1.1:1.1. Higher ratios of coupling agent and 5-aminotetrazole can be used but offer no advantages. Excesses of ten mole percent are satisfactory.

As those skilled in the art will recognize, all reactants can be added at once rather than in stepwise fashion as described above. However, prior formation of the reactive intermediate (acid-coupling agent product) normally produces better yields of desired N-(5-tetrazolyl)amides.

Alternatively, the desired amides may be synthesized by coupling the acids with 5-aminotetrazole using a mixed-anhydride procedure. In this case, the acids are first converted in situ to tertiary amine salt in the presence of a 1 to 1.1 molar excess of the amine. A variety of tertiary amines (R'$_3$N) are suitable for this purpose. Exemplary are triethylamine, N-methylpiperidine, N-methylmorpholine, dimethylaniline or quinoline. Suitable inert solvents are methylene chloride, chloroform, dimethylformamide, and dimethylacetamide. It is preferrable that the acid be completely dissolved by the excess of tertiary amine, which may require a stirring period, together with gentle warming, if necessary. The solution of amine salt is then reacted with an equivalent of alkyl (e.g. ethyl), benzyl, or phenyl chloroformate, at a temperature in the range of −40° to 25° C., preferably in the range −10° to 10° C., to form a mixed anhydride:

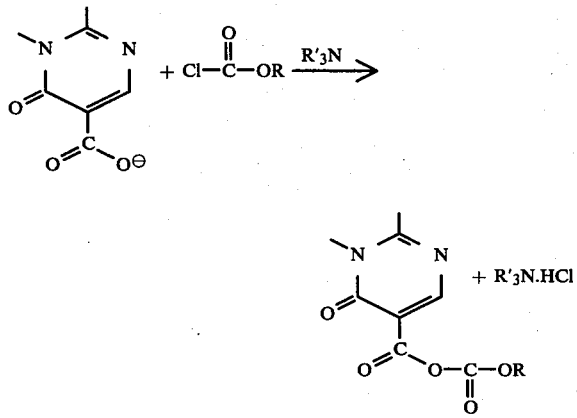

in solution. Without isolation, the mixed anhydride is reacted directly with 5-aminotetrazole, preferably dissolved in an inert solvent which is of the same type as that used to prepare the mixed anhydride, to yield the desired N-(5-tetrazolyl)amides. The reaction is usually initiated at a cool temperature (such as −40° to 15° C.), but allowed to warm to higher temperature (such as 15° to 40° C.) to complete the reaction. The typical molar ratio of acid:amine:chloroformate:5-aminotetrazole is 1:2:1:1 to 1:2.1:1.1:1.1.

Both the amides and the acids serve as intermediates for the pharmaceutically-acceptable cationic salts of this invention. Salt formation is accomplished by reacting the amides or acids with the appropriate metal salt (such as a carbonate, ethylhexanoate, alkoxide or hydroxide) or the appropriate amine in a suitable medium such as water, methanol or ethanol according to well-known procedures. The salts are recovered by standard methods such as by filtration if they are insoluble in the medium, by evaporation of the solvent if they are soluble in the medium, or by precipitation by addition of a non-solvent for the salt.

Many of the requisite 2-aminothiazole starting materials are described in the literature. Those which are not may be prepared by condensation of the appropriate alpha-haloketone with thiourea or by condensation of the appropriate aldehyde with thiourea and sulfuryl chloride, as illustrated in specific examples. Alpha-haloketones, when not available in the literature, are obtained by standard procedures, e.g. by halogenation of ketones [e.g. Catch et al., J. Chem Soc., 272 (1948); Levine, Org. Synthesis Coll. Vol. II, 88 (1943); Buchman et al., J. Am. Chem. Soc. 67, 400 (1945)], by the action of hydrogen halides on diazoketones [e.g. Ctch et al., J. Chem. Soc., 278 (1948); Lutz et al., J. Org. Chem. 12, 767 (1947); Wagner et al., J. Am. Chem. Soc. 72, 2884 (1950)], decarboxylation of alpha-halobeta-keto acids [McPhee et al., J. Am. Chem. Soc. 66, 1132 (1944)], and the spontaneous cleavage of the dibromo derivatives of alkenyl esters [e.g. Slanina et al., J. Am. Chem. Soc. 58, 891 (1936)].

The reactions in the synthetic sequence leading from 2-aminothiazoles to the acids and N-(5-tetrazolo) amides of the present invention are conveniently monitored by standard thin layer chromatography on silica gel plates containing an ultraviolet indicator, available commercially from a variety of sources. The eluant is varied to suit the reaction being carried out and the nature of the substituents, so as to obtain Rf values intermediate between 0 and 1.0, and so as to differentiate the intermediate going into the reaction and the product being produced in the reaction. Eluant particularly well-suited for thiazole formation, condensation cyclization and hydrolysis reactions in this application is chloroform/1% ethanol, while hydrolysis and conversion of acids to N-(5-tetrazolyl)amides is best monitored by use of chloroform/5% acetic acid. As is well-known to those skilled in the art, if materials tend to move too fast (i.e. in the solvent front) the polarity of the eluant can be reduced. If materials tend to move too slowly, polarity of the eluant can be increased. Such chromatography is used to assess completeness of reaction and purity, but can also be used to further optimize reaction conditions (concentration, time, temperature, solvent, etc.).

The products of this invention and the pharmaceutically acceptable salts thereof are useful as prophylactic agents to inhibit or prevent the release of mediators of anaphylaxis (allergy, immediate hypersensitivity reactions) and the occurrence of allergic symptoms in mammals, and can be administered for such uses individually or as mixtures with other agents; for example, with theophylline or sympathomimetic amines. The products of this invention are also useful as antiulcer agents. These products not only accelerate healing of such ulcers but also prevent formation of ulcers and decrease gastric acid output in animals, including humans. They can, therefore, be said to be useful for the control of gastric ulcers.

The valuable compounds of this invention can be administered alone, but are generally administered with a pharmaceutical carrier selected on the basis of the chosen route of administration and standard pharmaceutical practice. For example, they can be combined with various pharmaceutically-acceptable inert carriers in the form of tablets, capsules, lozenges, troches, hard candies, powders, aerosol sprays, aqueous suspensions or solutions, injectable solutions, elixirs, syrups and the like. Such carriers include solid diluents or fillers, sterile aqueous media and various non-toxic organic solvents. Moreover, the oral pharmaceutical compositions of this invention can be suitably sweetened and flavored by means of various agents of the type commonly used for this purpose.

The particular carrier selected and the proportion of active ingredient to carrier are influenced by the solubility and chemical nature of the therapeutic compounds, the chosen route of administration and the needs of standard pharmaceutical practice. For example, when the compounds of this invention are administered orally in tablet form, excipients such as lactose, sodium citrate, calcium carbonate and dicalcium phosphate can be used. Various disintegrants such as starch, alginic acids and certain complex silicates, together with lubricating agents such as magnesium stearate, sodium lauryl sulphate and talc, can also be used in producing tablets for the oral administration of these compounds. For oral administration in capsule form, lactose and high molecular weight polyethylene glycols are among the preferred materials for use as pharmaceutically-acceptable carriers. Where aqueous suspensions are to be used for oral administration, the compounds of this invention can be combined with emulsifying or suspending agents. Diluents such as ethanol, propylene glycol, glycerine and chloroform and their combinations can be employed as well as other materials.

For the purpose of parenteral administration and inhalation, solutions or suspensions of these compounds in sesame or peanut oil or aqueous propylene glycol solutions can be employed, as well as sterile aqueous solutions of the soluble pharmaceutically-acceptable salts described herein. These particular solutions are especially suited for intramuscular and subcutaneous injection purposes should such method of administration be desired. The aqueous solutions, including those of the salts dissolved in pure distilled water, are also useful for intravenous injection purposes provided that their pH is properly adjusted beforehand. Such solutions should also be suitably buffered, if necessary, and the liquid diluent first rendered isotonic with sufficient saline or glucose.

When used as prophylactic agents to prevent the release of mediators of anaphylaxis, the compounds can be administered by inhalation. Compositions suitable for inhalation can comprise (1) a solution or suspension of the active ingredient in a liquid medium of the type mentioned above for administration via a nebulizer; (2) a suspension or solution of the active ingredient in a liquid propellant such as dichlorodifluoromethane or chlorotrifluoroethane for administration from a pressurized container; or (3) a mixture of the active ingredient and a solid diluent (e.g. lactose) for administration from a powder inhalation device. Compositions suitable for inhalation by means of a conventional nebulizer will comprise about 0.1 to about 1% of active ingredient; and those for use in pressurized containers will comprise from about 0.5 to about 2% of active ingredient. Compositions for use as powder inhalants can comprise ratios of active ingredient to diluent of from about 1:0.5 to about 1:1.5.

Having full regard for the foregoing factors, it is considered that an effective daily oral dosage of the antiallergy or antiulcer compounds of the present invention in humans is from about 10 to about 1500 mg. per day, with a preferred range of about 10 to about 600 mg. per day in single or divided doses, or at about 0.2 to about 12 mg./kg. of body weight. These values are illustrative and there may, of course, be individual cases where higher or lower dose ranges are merited. With careful supervision, the dosage level can range up to as high as about 2 grams per day.

When administered parenterally for either use, or by inhalation as an antiallergy agent, the effective daily dose is from about 0.05 to about 400 mg. per day, and preferably from about 0.25 to 200 mg. per day, or at about 0.005 to 4 mg./kg. of body weight in a single or divided dose.

It is necessary that the active ingredient form a proportion of the composition such that a suitable dosage form will be obtained. Obviously, several dosage unit forms can be administered at about the same time. Although compositions with less than 0.005% by weight of active ingredient might be used in certain instances, it is preferred to use compositions containing not less than 0.005% of the active ingredient; otherwise, the amount of carrier becomes excessively large. Activity increases with the concentration of the active ingredient. The composition may contain 10, 50, 75, 95 or an even higher percentage by weight of the active ingredient.

The PCA test is a measure of the anti-allergic (especially anti-asthmatic) activity of a compound. Compounds which inhibit a positive PCA test induced by the rat immunochemical counterpart of human immunoglobulin E (IgE), or reagin, are considered to have anti-allergic activity (C. Mota, Ann. N.Y. Acad. Sci., 103, 264 1963). (Reagin is primarily immunoglobulin E [IgE] and is the principal immunoglobulin responsible for allergic asthma, anaphylaxis, hay fever, food sensitivities and certain manifestations of drug sensitivities, although recent evidence ascribes to the IgG class of antibodies a significant role in the mediation of allergic diseases). Such compounds when administered to a sensitized subject, human or animal, prior to the time when the subject comes into contact with antigens or substances to which it is allergic, will prevent the allergic reaction which would otherwise occur. They, therefore, provide a method for the prophylactic treatment of allergy or anaphylactic reactions of a reagin mediated nature.

To put it another way, such compounds block the release of mediators resulting from the antigen-antibody (allergic) reaction as illustrated in the PCA test using rat homocytotropic antibody—a known correlate of human reaginic antibody. Inhibition of reaginic antigen-antibody reactions in rats, the test animal of the PCA test, is regarded as representative of inhibition of human reaginic antigen-antibody reactions which occur during allergic episodes.

The PCA reaction test procedure employed to evaluate the compounds of the present invention demonstrates an excellent correlation between activity for compounds in this test and their utility in the treatment of allergic asthma. The ability of agents to interfere with PCA reactions is measured in male Charles River Wistar rats, 170–210 g. Reaginic antiserum, rich in IgE antibodies, is prepared according to Petillo et al., Int. Arch. Allergy, 44, 309 (1973). Hyperimmune antiserum rich in IgG antibodies to hen egg albumin is prepared according to Orange et al., J. Exptl. Med., 127, 767 (1968). Forty-eight hours prior to antigen challenge, the reaginic antiserum is injected intradermally (i.d.) into the shaved skin of a normal rat's back; 5 hours before challenge the hyperimmune antisera is similarly injected. At a third site 60 mcg. histamine dihydrochloride and 0.5 mcg. serotonin creatinine sulfate are injected i.d. just prior to antigen challenge as a check for antihistaminic, antiserotonin and unspecific types of blockage; the compounds of the instant invention or saline are then administered i.v. and immediately followed by the challenge of 5 mg. egg albumen and 2.5 mg. Evans' Blue dye in saline. In the case of oral administration Evans' Blue dye and egg albumin are given 5 minutes after administration of the drug. Thirty minutes later the animals are asphyxiated using chloroform and the skin of the back removed and reversed for observation. A score is assigned each injection site equal to the product of the diameter of the site in mm. and a grade of 0.1, 0.5, 1, 2, 3 or 4 proportional to intensity of dye coloration. The scores for a given injection site are summed for each group of five animals and compared to the saline treated controls. The difference is expressed as percent blockage due to the compound employed.

Compounds representative of those of the present invention are tested for antiallergy activity by the above-described procedure and the resulting activities are reported as the degree (%) of protection. Intal, disodium cromoglycate, a commercial antiallergy agent is not included for comparison, since it is not active by the oral route.

The compounds of the formula I (amides) and II (acids, $R_3$ is hydrogen) tested for antiallergy activity by the PCA test are detailed in Tables I and II.

TABLE I

Oral Activity (% of Protection) of Amides (Formula I) in the PCA Test

| $R_1$ | $R_2$ | IgE mg./kg. 1 | 3 | 10 | 30 | IgG mg./kg. 1 | 3 | 10 | 30 |
|---|---|---|---|---|---|---|---|---|---|
| $CH_3$ | $CH_3$ | | 55 | | | | 51 | | |
| $CH_3$ | $C_2H_5$ | | | 75 | | | | 57 | |
| $C_2H_5$ | $CH_3$ | | | 29 | | | | 28 | |
| $C_2H_5$ | $C_2H_5$ | | | 62 | | | | 49 | |
| | $(CH_2)_3$ | 46 | | | | 43 | | | |
| | $(CH_2)_4$ | | 47 | | | | 45 | | |
| | $(CH_2)_5$ | | | 25 | | | | 38 | |
| | $(CH_2)_6$ | | | 94 | | | | 57 | |
| H | $CH_3$ | | 55 | | | | 50 | | |
| H | H | | | 50 | | | | 46 | |
| $CH_3$ | H | | | 78 | | | | 55 | |
| $C_2H_5$ | H | | | 85 | | | | 58 | |
| H | $C(CH_3)_3$ | | | 37 | | | | 20 | |
| H | $C_2H_5$ | | | 70 | | | | 44 | |
| H | $CH(CH_3)_2$ | | | 72 | | | | 53 | |
| $CH_2CH(C_5H_6)CH_2CH_2$ | | | | 4 | | | | 7 | |
| $CH_2CH(CH_3)CH_2CH_2$ | | | | 44 | | | | 33 | |
| $CH_2C(CH_3)_2CH_2CH_2$ | | | | 38 | | | | 27 | |
| H | CHCH$_2$CH$_3$<br>\|<br>CH$_3$ | | | 6 | | | | 6 | |

TABLE II

Oral Activity (% of Protection) of Acids (Formula II; $R_3$ is Hydrogen) in the PCA Test

| $R_1$ | $R_2$ | IgE mg./kg. 10 | 30 | IgG mg./kg. 10 | 30 |
|---|---|---|---|---|---|
| $CH_3$ | $CH_3$ | | 0 | | 0 |
| $CH_3$ | $C_2H_5$ | | 0 | | 0 |
| $C_2H_5$ | $CH_3$ | | 42 | | 24 |
| $C_2H_5$ | $C_2H_5$ | | 41 | | 32 |
| | $(CH_2)_3$ | | 0 | | 0 |
| | $(CH_2)_4$ | 55 | | 39 | |
| | $(CH_2)_5$ | | 37 | | 44 |
| | $(CH_2)_6$ | 36 | 68 | 15 | 45 |
| H | $CH_3$ | | 18 | | 19 |
| H | H | | 18 | | 7 |
| $CH_3$ | H | | 12 | | 14 |
| $C_2H_5$ | H | | 45 | | 38 |
| H | $C(CH_3)_3$ | | 10 | | 6 |
| H | $C_2H_5$ | | 13 | | 21 |
| H | $CH(CH_3)_2$ | | 0 | | 0 |
| $CH_2CH(C_5H_6)CH_2CH_2$ | | | 15 | | 5 |
| $CH_2CH(CH_3)CH_2CH_2$ | | | 31 | | 21 |
| $CH_2C(CH_3)_2CH_2CH_2$ | | | 13 | | 6 |
| H | CHCH$_2$CH$_3$<br>\|<br>CH$_3$ | | 1 | | 8 |

The effectiveness of the products of this invention as anticulcer agents is determined by the so-called cold-restraint stressed rat assay. In this test nonfasted female rats (Charles River C-D strain) weighing 70-140 gms. are administered the drug or carrier (control animals) intraperitoneally (in saline solution containing 1% carboxymethylcellulose and 0.1% Tween 80) or orally (in water) three hours before being lightly anesthetized with ether and taped in the supine position to individual sheets of plexiglass. After recovery from anesthesia, the restrained animals are positioned horizontally in a refrigerator maintained at 10°-12° C. and three hours later sacrificed by cervical dislocation. The abdomen of each rat is opened, the pylorus clamped, the stomach inflated with saline via an oral tube, the esophagus clamped and the stomach excised. The stomachs are placed in a 0.4% formaldehyde solution for approximately 30 seconds to harden the outer layers and facilitate examination. Each stomach is then cut open along the greater curvature and the glandular portion (hind stomach) examined for damage. The number of gastric erosions, their severity and the color of the stomachs is recorded. The Mann-Whitney-Wilcoxan rank sum test is used to compare the median number of gastric erosions in the control group with the median number of gastric erosions in each drug-treated group to determine if they are statistically different. (Dixon et al., "Introduction to Statistical Analysis," 3rd Ed., McGraw-Hill Book Company, New York, pp. 344-347, 1969). In this test N-(5-tetrazolyl)-thiazolo[3,2-a]pyrimidine 2-carboxamide (compound III) is extremely potent as detailed below.

Alternatively, the effectiveness of the products of this invention as antiulcer agents is determined in an ethanol-induced rat ulcer assay. In this test, overnight fasted male rats are given drug (5 mg./kg.) or water orally fifteen minutes prior to an orally administered dose of absolute ethanol (1.0 ml.). One hour after the ethanol challenge the animals (8/group) are killed and the stomachs examined for the presence of lesions. All drugs were dissolved in dilute NaOH. After sacrifice the abdomen is opened and a locking hemostat placed at the pylorus. 6 ml. of a 4% solution of formaldehyde was injected into the stomach with a gastric feeding tube and a second locking hemostat was used to seal the esophagus. The stomach was removed, opened along the greater curvature and examined for ulceration.

The scoring system used to quantitate the ethanol-induced lesions is given below.

| Ulcer Score Table | |
|---|---|
| Score | Definition |
| 1 | Normal appearing stomach |
| 2 | Pinpoint sized lesions. |
| 3 | Lesions, 2 or fewer; pinpoint lesions may be present. |
| 4 | Lesions, >2; pinpoint lesions may be present. |
| 5 | Lesions with hemorrhage. |

For each group of animals an ulcer index is calculated as follows:

Ulceration Index = (the sum of the scores of the group) × (the sum of the number of ulcers in the group) × (the fraction of the group having any incidence of ulceration).

The percentage inhibition of ulcers is calculated as follows:

% Inhibition = 100 × [(ulcer index controls) − (ulcer index drug-treated)] ÷ (ulcer index controls).

Table III shows the activity in this test of various 5-tetrazolylamides of this invention, while Table IV shows the activity of various acids.

TABLE III

Oral Activity (% of Inhibition at 5 mg./kg. dosage) of Amides(Formula I) in the Ethanol-Induced Rat Ulcer Assay

| $R_1$ | $R_2$ | % Inhibition |
|---|---|---|
| $CH_3$ | $CH_3$ | 96 |
| H | $CH_3$ | 59 |

TABLE III-continued
Oral Activity (% of Inhibition at 5 mg./kg. dosage) of Amides(Formula I) in the Ethanol-Induced Rat Ulcer Assay

| $R_1$ | $R_2$ | % Inhibition |
|---|---|---|
| $CH_3$ | H | 72 |
| $C_2H_5$ | $C_2H_5$ | 10 |
| $C_2H_5$ | H | 86 |
| $(CH_2)_6$ | | 45 |
| $(CH_2)_4$ | | 97, 81 |

TABLE IV
Oral Activity (% Inhibition at 5 mg./kg. Dosage) of Acids (Formula II) in the Ethanol-Induced Rat Ulcer Assay

| $R_1$ | $R_2$ | % Inhibition |
|---|---|---|
| $CH_3$ | $CH_3$ | 11 |
| H | $CH_3$ | 27 |
| $CH_3$ | H | 0 |
| $C_2H_5$ | $C_2H_5$ | 48 |
| $C_2H_5$ | H | 48 |
| $(CH_2)_4$ | | 21 |

As has been previously noted, the most highly preferred of the compound of this invention is of the formula III, i.e., formula I, wherein $R_1$ and $R_2$ taken together are butylene [N-(5-tetrazoyl)-1-oxo-1H-cyclohexenothiazolo[3,2-a]pyrimidine-2-carboxamide, which may alternatively be named 5,6,7,8-tetrahydro-N-(5-tetrazolyl)-4-oxo-4-H-pyrimido(2,1-b)benzothiazole-3-carboxamide].

In addition to its oral antiallergenic activity shown in Table I, compound III shows intravenous activity in the range 0.03-1.0 mg./kg. in the PCA test, being some 26 times more potent than Intal by this route (as previously noted, Intal lacks efficacy by the oral route). Compound III also blocks the changes in cutaneous permeability induced by an IgE-mediated passive cutaneous anaphylaxis (PCA) but does not interfere with the changes in permeability caused by intradermal injection of exogeneous histamine and serotonin. The absence of antihistaminic and antiserotonin effects demonstrates that the antiallergy mechanism is one of inhibition of mediator release rather than antagonism at the mediator receptor.

Compound III inhibits dextran induced release of histamine into the rat peritoneal cavity. Its $ED_{50}$ is 0.33 $\mu$g/kg, i.p. and that of Intal is 14.0 $\mu$g/kg, demonstrating the superior potency of the former. The rise in plasma histamine caused by antigen challenge to rats passively sensitized with IgE-rich antiserum (passive systemic anaphylaxis is prevented by compound III. Its $ED_{50}$ is 28 $\mu$g/kg, i.v., 13 times more potent than Intal.

Guinea pigs dosed with compound III, 30 mg/kg i.p., were not protected against the brochoconstrictive effects of inhaled histamine. In the concentration range $10^{-8}$ to $10^{-4}$ M, III does not antagonize spasms of isolated guinea pig ileum induced with acetylcholine, histamine or slow reacting substance of anaphylaxis (SRS-A) and the synthesis and release of SRS in isolated rat monocytes, stimulated by an ionophore is not inhibited by III.

In addition to its potent activity in the ethanol-induced rat ulcer assay (see Table III above), Compound III is highly potent in the cold-restraint stress gastric ulcer procedure (detailed above), where it provides dose-related protection at oral doses in the range 3 to 100 $\mu$g./kg. Compound III also protects against the ulcerogenic effects of aspirin, 100 mg/kg p.o. where dose-related effects are seen over the dose range of 10 to 1000 $\mu$g/kg, p.o. with an $ED_{50}$ of 100 $\mu$g/kg. Compound III is also active in a phenylbutazone gastric ulcer model where an oral $ED_{50}$ of 200 $\mu$g/kg is observed. Although III is a highly potent antiulcer agent, it does not affect pentagastrin-stimulated acid output in Heidenhain pouch dogs (5 mg/kg, i.v.) and is, therefore, distinct from the anti-secretory prostaglandins, and from cimetidine and atropine. "Cytoprotective," a term coined recently to describe the antiulcer effects of prostaglandins that are independent of antisecretory activity, [Robert, Advances in Prostaglandin and Thromboxane Research 2, 507 (1976); Miller et al., Gut 20, 75 (1979); Robert et al., Gastroenterology 72, 1121 (1977).] aptly characterizes the effects of compound III.

Furthermore, compound III exhibits diuretic activity. When given orally, it caused a dose-related increase in urinary volume output at doses in the range 0.3 to 5 mg/kg. The maximum effect was a twofold increase in volume output. The urinary concentrations of sodium and potassium ions were unchanged but, because of the increase in volume output, an increase in sodium and potassium excretion was observed. These findings indicate that the dose-response range for diuretic activity is considerably higher than that for antiulcer effects and just below that for antiallergy effects (1 to 10 mg/kg).

Rats, fasted for 24 hours and dosed orally with III at doses of 10, 30 or 100 mg/kg, did not exhibit any changes in blood glucose levels.

The effect of III on glucose tolerance was examined in rats given 10, 30, or 100 mg/kg p.o. simultaneously with glucose, 1 g/kg, p.o. An apparent dose-dependent improvement in glucose tolerance was observed. This effect may be due to a delayed absorption of glucose related to a possible effect on gastric emptying.

Compound III has no significant anticholinergic effects. In anesthethized dogs at cumulative doses of 5 and 15 mg/kg, i.v., caused transient hypotension and variable changes in heart rate. Pressor responses to epinephrine and bilateral carotid occlusion were diminished slightly. The transient cardiovascular changes occur only at cumulative intravenous doses which are 5 to 15 fold higher than the maximally effective intravenous dose for antiallergy effects and very much higher than the oral doses required for antiulcer effects.

In toleration studies, III was given orally by gavage to dogs for a period of seven days at doses of 50, 150 and 300 mg/kg/day. Emesis, which is common in dogs, was observed at all doses but subsequent studies revealed that the emetic effect could be eliminated if the drug were administered by capsule after, rather than before, meals. No gross pathological changes were observed and microscopic examination of the liver, kidney, heart and lung did not reveal any changes. In other studies, the serum enzyme levels of dogs, given III intravenously for five days at consecutive daily doses of 1, 3, 10, 3 and 3 mg/kg, remained normal.

Rats were given III orally by gavage at doses of 50, 150 and 300 mg/kg/day for 10 days. There were no resultant pathological changes on gross and microscopic evaluation of liver, kidney, heart and lung. Apart from a slight increase in serum glutamic-pyruvic transaminase observed at the highest dose, no changes in clinical chemistry were observed.

Compound III was administered subcutaneously to mice at doses of 100, 300 or 1000 mg/kg. No symptoms or lethality was observed and it is concluded that the drug is well tolerated acutely with a subcutaneous LD$_{50}$>1000 mg/kg. At a dose of 32 mg/kg given subcutaneously, no interactions with a battery of CNS-active drugs were observed.

Single oral doses of III, 40 mg/kg, were administered to groups of mice who were sacrificed 6, 12 or 24 hours later. Microscopic examination of bone marrow did not reveal any chromosomal damage. Similar findings were made when mice were treated for five consecutive days with a dose of 20 mg/kg. In vitro studies in which III was incubated with human lymphocytes at concentrations of 1000, 100, 10 or 0 µg/ml also failed to reveal any significant drug-induced chromosomal breakage. Compound III in the Ames test in vitro, did not induce point mutations. From these findings, it is evident that III has no obvious mutagenic potential.

In the rat PCA test, the ratio of comparably effective oral and intravenous doses of III is consistent with good oral absorption. This is supported by the observations of plasma concentrations of 3 to 7 µg/ml one hour after oral administration of III, 50 to 300 mg/kg. In dogs, the drug appears to be absorbed readily after oral administration of suspensions or capsules, achieving plasma concentrations of 9 to 26 µg/ml one hour after oral doses of 50 to 300 mg/kg. In both species, plasma levels of the corresponding carboxylic acid metabolite (the corresponding compound of formula II) are comparable to those of III, identifying this compound as an important metabolite of III. After the eighth daily dose, the levels of parent drug and metabolite were 2 to 4 times greater than after the initial dose, suggesting that it is possible to maintain therapeutic drug levels for prolonged periods.

Compound III, in the solid state alone, or admixed with standard inert ingredients used in oral formulations, on in solution, shows exceptionally good stability, rendering facile the preparation of stable formulations of this compound for clinical use.

The following examples are provided solely for the purpose of illustration and are not to be construed as limitations of this invention, many variations of which are possible without departing from the spirit or scope thereof.

EXAMPLE 1

2-Amino-4-ethyl-5-methylthiazole

Thiourea (20.9 g., 0.275 mole) was dissolved in 250 ml. of refluxing ethanol. 2-Bromo-3-pentanone (41.3 g., 0.25 mole) dissolved in 50 ml. of ethanol was added dropwise over 25 minutes to the refluxing urea solution. Following an additional 2 hours of reflux, the reaction was boiled down to approximately 100 ml., cooled and the crude product recovered as the hydrobromide salt by filtration. Purified 2-amino-4-ethyl-5-methyltetrazole (15.1 g.; m.p. 45°-50° C.; m/e calcd: 142; found: 142) was obtained by dissolution in water and reprecipitation with aqueous 3 N potassium hydroxide.

By the same method, 1-bromo-2-heptanone, 3-bromo-4-heptanone and 4-bromo-2,5-dimethyl-3-hexanone are converted to 2-amino-4-pentylthiazole, 2-amino-4-ethyl-5-propylthiazole and 2-amino-4,5-diisopropylthiazole, respectively.

EXAMPLE 2

2-Amino-4,5-diethylthiazole hydrochloride

Thiourea (21.8 g., 0.286 mole), 4-chloro-3-hexanone (34.4 g., 0.26 mole) and 200 ml. of ethanol were combined and heated to reflux for 19 hours. The reaction mixture was cooled and stripped of solvent to yield the crude product as a white solid. White crystals of 4,5-diethylthiazole hydrochloride (31 g., m.p. 154°-156° C.) were obtained by recrystallization from a mixture of ethyl acetate and ethanol.

EXAMPLE 3

2-Amino-cycloheptenothiazole

Thiourea (41.9 g., 0.55 mole), 2-chlorocycloheptanone (72.3 g., 0.49 mole) and 500 ml. of ethanol were combined and refluxed for 7 hours. The solvent was stripped, leaving a semi-solid which was distributed between ethyl acetate and water. Unreacted chloroketone, recovered from ethyl acetate phase by stripping, was combined with 20 g. of thiourea and ethanol, refluxed for 24 hours, stripped and additional crude product distributed between ethyl acetate and water as above. In each case, product was recovered by making the aqueous phase basic with ammonium hydroxide, extraction into ethyl acetate, drying over anhydrous sodium sulfate, stripping to an oil, solidification by trituration with hexane and filtration. Purified 2-aminocycloheptenothiazole (49.5 g., m.p. 77°-78.5° C.) was obtained by recrystallization from cyclohexane.

EXAMPLE 4

2-Amino-4-isopropylthiazole

Thiourea (52.5 g., 0.69 mole) was slurried in 400 ml. of ethanol. 1-Bromo-3-methyl-2-butanone (109.5 g., 0.66 mole) was added to the slurry. The resulting exothermic reaction caused dissolution and reflux. Reflux was maintained by external heating for one hour. Solvent was removed by boiling and stripping to yield an oil which crystallized on standing. Final purification of 2-amino-4-isopropylthiazole hydrobromide (104.4 g., m.p. 74°-76° C.) was achieved by trituration with ether.

The hydrobromide salt was converted to free base (58.6 g.) by dissolving the salt in water, basifying with excess ammonium hydroxide, extracting the free base into ether, drying the ether over anhydrous sodium sulfate and stripping to an oil.

EXAMPLE 5

2-Amino-6-phenylcyclohexenothiazole

Thiourea (397. 5 mg., 5.22 mmoles) was slurried in 6 ml. of ethanol. 2-Bromo-4-phenylcyclohexanone (1.2 g., 4.74 mmoles) was added to the slurry, resulting in an exothermic reaction and dissolution. The solution was refluxed for 30 minutes, cooled and the solvent stripped to yield crude product as the hydrobromide salt.

This crude salt was dissolved in warm water, filtered and the free base precipitated by the addition of ammonium hydroxide. Crude base was recovered by filtration and purified 2-amino-6-phenylcyclohexenothiazole (802.4 mg., m.p. 181°-183° C.) obtained by recrystallization from a mixture of water and ethanol.

Alternatively, on a larger scale employing 8.2 g. of thiourea, 24.6 g. of 2-bromo-4-phenylcyclohexenone and 125 ml. of ethanol, the reaction mixture, following the 30 minute reflux period, was chilled in an ice bath and the hydrobromide salt recovered directly by filtration. The hydrobromide salt was dissolved in water containing a trace of ethanol by heating and the free base (10.4 g., m.p. 180°-182° C.) precipitated by the addition of excess ammonium hydroxide.

By the same methods, 2-bromo-3-phenylcyclopentanone, 2-bromo-3,5-dimethylcyclohexanone, 2-bromo- 3,5,5-trimethylcyclopentanone and 2-bromo-5-methylcyclooctanone are converted to either the hydrobromide salt or the free base of 2-amino-6-phenylcyclopentenothiazole, 2-amino-5,7-dimethylcyclohexeneothiazole, 2-amino-4,4,6-trimethylcyclopentenothiazole and 2-amino-7-methylcyclooctenothiazole, respectively.

EXAMPLE 6

2-Amino-6-methylcyclohexenothiazole

Thiourea (22.3 g., 0.29 mole) was slurried in 275 ml. of ethanol. 2-Bromo-4-methylcyclohexanone was added and the mixture heated to reflux for 75 minutes. The reaction mixture was cooled to room temperature and the crude product recovered as the hydrobromide salt by filtration. The crude salt was dissolved in warm water, filtered and made basic with ammonium hydroxide to precipitate the free base as an oil, which crystallized on cooling. Purified 2-amino-6-methylcyclohexenothiazole (25.2 g., m.p. 98°–100° C.) was obtained by recrystallization from cyclohexane.

EXAMPLE 7

2-Amino-6,6-dimethylcyclohexenothiazole

2-Amino-6,6-dimethylcyclohexenothiazole (9.8 g., m.p. 109°–111° C.) was made from thiourea (9.2 g., 0.12 mole) and 2-bromo-4,4-dimethylcyclohexanone (22.6 g., 0.11 mole) in 100 ml. of ethanol according to the method of example 6.

EXAMPLE 8

2-Amino-4-(2-butyl)thiazole

Thiourea (16.7 g., 0.22 mole), 1-bromo-3-methyl-2-pentanone (36 g., 0.2 mole) and 100 ml. of ethanol were combined and heated to reflux for 5 hours. Aqueous potassium hydroxide (3 N, 100 ml.) was added and reflux continued for an additional 0.5 hour. The reaction mixture was cooled, acidified with hydrochloric acid and non-basic impurities extracted away with ether. The aqueous phase was made basic with ammonium hydroxide and the product extracted into ether. Following back-wash with water and drying over anhydrous sodium sulfate, the ether was stripped to yield 10 g., of 2-amino-4-(2-butyl)thiazole as a dark brown viscous oil.

EXAMPLE 9

2-Amino-5-methylthiazole

Thiourea (45.7 g., 0.6 mole) and propionaldehyde (7.4 g., 0.3 mole) were combined with 150 ml. of chloroform and cooled in an ice bath. Sulfuryl chloride (44.5 g., 0.33 mole) was added over 15 minutes. The exothermic reaction was maintained between 15° and 24° C. Gassing, which occurred during addition, ceased about 1 hour after addition was complete. Most of the chloroform was boiled off on a steam bath. Ethanol (150 ml.) was added and the mixture refluxed for 3 hours.

The reaction was stripped to an oil, which was distributed between water and ethyl acetate. The aqueous phase was made basic with ammonium hydroxide and the product extracted into fresh ethyl acetate. The ethyl acetate was dried over anhydrous sodium sulfate and stripped to yield crude product as a white solid. Purified 2-amino-5-methylthiazole (8.36 g., m.p. 94°–95° C.) was obtained by recrystallization from cyclohexane.

EXAMPLE 10

2-Amino-5-ethylthiazole

Thiourea (45.7 g., 0.6 mole) and butyraldehyde (21.6 g., 0.3 mole) were combined with 150 ml. of chloroform and cooled in an ice bath. Sulfuryl chloride (44.5 g., 0.33 mole) was added over 15 minutes. The exothermic reaction was maintained between 15° and 25° C. Gassing occurred during addition and for about 1 hour thereafter. Ethanol (400 ml.) was added, the chloroform was boiled off and the reaction mixture refluxed overnight (approximately 16 hours.). The reaction was stripped to an oil and recrystallized 2-amino-5-ethylthiazole (11.7 g., m.p. 54°–55° C.) isolated by the method of example 9.

By the same method, pentanal, 3-methylbutanal and heptanal are converted to 2-amino-5-propylthiazole, 2-amino-5-isopropylthiazole and 2-amino-5-pentylthiazole, respectively.

EXAMPLE 11

2-(2,2-Dicarbethoxyethenylamino)-4,5-dimethylthiazole

2-Amino-4,5-dimethylthiazole (2.56 g., 20 mmoles), diethyl ethoxymethylenemalonate (4.8 g., 22 mmoles) and ethanol (5 ml.) were refluxed for 1 hour. The reaction mixture was cooled and the crude product precipitated with hexane. Purified 2-(2,2-dicarbethoxyethenylamino)-4,5-dimethylthiazole (4.21 g., m.p. 82°–83.5° C.) was obtained by recrystallization from hexane.

EXAMPLE 12

2-(2,2-Dicarbethoxyethenylamino)-4-ethyl-5-methylthiazole

2-Amino-4-ethyl-5-methylthiazole (2.84 g., 20 mmoles) and diethyl ethoxymethylenemalonate (4.76 g., 22 mmoles) were combined and heated on a steam bath for 3 hours. The product, obtained as an oil by cooling, was used without further purification in the subsequent step.

By the same method, 2-amino-4-pentylthiazole, 2-amino-4-propyl-5-ethylthiazole, 2-amino-4,5-diisopropylthiazole, 2-amino-5-propylthiazole, 2-amino-5-isopropylthiazole, 2-amino-5-pentylthiazole, 2-amino-6-phenylcyclopentenothiazole, 2-amino-5,7-dimethylcyclohexenothiazole, 2-amino-4,6,6-trimethylcyclopentenothiazole, and 2-amino-7-methylcyclooctenothiazole are converted to the corresponding 2-(2,2-dicarbethoxyethenylamino)thiazole derivatives.

By the same method, the corresponding dimethyl, dipropyl and diisopropyl esters are prepared by substituting the appropriate dimethyl, dipropyl or diisopropyl ethoxymethylenemalonate for diethyl ethoxymethylenemalonate.

EXAMPLE 13

2-(2,2-Dicarbethoxyethenylamino)-4-methyl-5-ethylthiazole

4-Methyl-5-ethylthiazole (5.68 g., 40 mmoles) and diethyl ethoxymethylenemalonate (9.52 g., 44 mmoles) were heated briefly to 86° C. and then cooled to yield the product as an oil, used directly in the next step.

EXAMPLE 14

2-(2,2-Dicarbethoxyethenylamino)-4,5-diethylthiazole

Diethylthiazole hydrochloride (15.4 g., 80 mmoles), diethyl ethoxymethylenemalonate (19.0 g., 88 mmoles), triethylamine (8.1 g., 80 mmoles) and ethanol (125 ml.) were combined and refluxed for 2.5 hours. The reaction mixture was cooled and stripped of solvent. The resulting semisolid product was distributed between ethyl acetate and water. The 2-(2,2-dicarbethoxyethenylamino)-4,5-diethylthiazole (28.6 g.) was obtained as a golden oil from the ethyl acetate phase by drying over anhydrous sodium sulfate and stripping.

By the same method, the hydrobromide salts of 5,7-dimethylcyclohexenothiazole, 4,4,6-trimethylcyclopentenothiazole and 7-methylcyclootenothiazole are converted to the corresponding 2-(2,2-dicarbethoxyethenylamino)thiazole derivatives.

By the same method, the corresponding dimethyl, dipropyl and diisopropyl esters are prepared by substituting the appropriate dimethyl, dipropyl or diisopropyl ethoxymethylenemalonate for diethyl ethoxymethylenemalonate.

EXAMPLE 15

2-(2,2-Dicarbethoxyethenylamino)cyclopentenothiazole

2-Aminocyclopentenothiazole (3.6 g., 34.5 mmoles) and diethylethoxymethylenemalonate (8.2 g., 38.0 mmoles) were combined and heated on a steam bath for 100 minutes. The reaction was cooled and 2-(2,2-dicarbethoxyethenylamino)cyclopentenothiazole (7.0 g., Rf 0.6 on silica gel thin layer chromatography with chloroform/1% ethanol as eluant) crystallized by the addition of hexane.

EXAMPLE 16

2-(2,2-Dicarbethoxyethenylamino)cyclohexenothiazole

2-Aminocyclohexenothiazole (7.7 g., 50 mmoles) and diethylethoxymethylenemalonate (11.9 g., 55 mmoles) were combined with 10 ml. of ethanol and refluxed for 50 minutes. The reaction mixture was cooled and 2-(2,2-dicarbethoxyethenylamino)cyclohexenothiazole (15 g., Rf 0.5 on silica gel thin layer chromatography with chloroform/1% ethanol as eluant) precipitated by the addition of 50 ml. of hexane.

Alternatively, 58.4 g. of 2-aminocyclohexenothiazole, 89.82 g. of diethyl ethoxymethylenemalonate and 584 ml. of cyclohexane were combined and refluxed under nitrogen for 2.5 hours, cooled to 15° C., and product (96 g., m.p. 113° C.) recovered by filtration.

EXAMPLE 17

2-(2,2-Dicarbethoxyethenylamino)cyclooctenothiazole

2-Aminocyclooctenothiazole (2.0 g., 11 mmoles) and diethylthoxymethylenemalonate (2.62 g., 12.1 mmoles) were combined and heated on a steam bath for 2.75 hours. The reaction mixture was cooled and 2-(2,2-dicarbethoxyethenylamino)cyclooctenothiazole (3.13 g., Rf 0.6 on silica gel chromatography with chloroform/1% ethanol as eluant) precipitated by the addition of hexane.

EXAMPLE 18

2-(2,2-Carbethoxyethenylamino)-4-methylthiazole

2-Amino-4-methylthiazole (4.57 g., 40 mmoles) and diethyl ethoxymethylenemalonate (9.51 g., 44 mmoles) were combined and heated on a steam bath for 1 hour. The reaction mixture was cooled and 2-(2,2-dicarbethoxyethenylamino)-4-methylthiazole (9.8 g., Rf 0.5 on silica gel thin layer chromatography with chloroform/1% ethanol as eluant) precipitated by the addition of 60 ml. of hexane.

EXAMPLE 19

2-(2,2-Dicarbethoxyethenylamino)thiazole

2-Aminothiazole (10.0 g., 0.10 mole) and diethyl ethoxymethylenemalonate (23.8 g., 0.11 mole) were combined and heated on a steam bath for 1.25 hours. The reaction mixture was cooled and the resulting semisolid recrystallized from hexane to yield purified 2-(2,2-dicarbethoxyethenyl)thiazole (17.2 g. in two crops, Rf 0.6 on silica gel thin layer chromatography with chloroform/1% ethanol as eluant).

EXAMPLE 20

2-(2,2-Dicarbethoxyethenylamino)-5-methylthiazole

2-Amino-5-methylthiazole (6.85 g., 60 mmoles) and diethyl ethoxymethylenemalonate (14.3 g., 66 mmoles) were heated on a steam bath for 1 hour. The reaction mixture was cooled and the product precipitated by the addition of approximately 75 ml. of hexane. Purified 2-(2,2-dicarbethoxyethenylamino)-5-methylthiazole (14.1 g. in two crops, Rf 0.55–0.65 on silica gel thin layer chromatography with chloroform/1% ethanol as eluant) was obtained by recrystallization from hexane.

EXAMPLE 21

2-(2,2-Dicarbethoxyethenylamino)-5-ethylthiazole

2-Amino-5-ethylthiazole (11.7 g., 91.3 mmoles) and diethyl ethoxymethylenemalonate (21.7 g., 100.43 mmoles) were combined and heated on a steam bath for 45 minutes. 2-(2,2-Dicarbethoxyethylamino)-5-ethylthiazole (27.2 g., Rf 0.6 and 0.7 respectively, on silica gel thin layer chromatography, with chloroform/1% ethanol and with 2:1 hexane:ethyl acetate as eluant) was obtained as an oil by cooling and used directly in the next step.

EXAMPLE 22

2-(2,2-Dicarbethoxyethenylamino)-4-(2-methyl-2-propyl)thiazole

2-Amino-4-(2-methyl-2-propyl)thiazole (15.6 g., 0.1 mole) and diethyl ethoxymethylenemalonate (23.8 g., 0.11 mole) were combined and heated on a steam bath for 2 hours. 2-(2,2-Dicarbethoxyethenylamino)-4-(2-methyl-2-propyl) thiazole was obtained as a wet solid on cooling and used directly in the next step.

EXAMPLE 23

2-(2,2-Dicarbethoxyethenylamino)-4-ethylthiazole

2-Amino-4-ethylthiazole (20.5 g., 0.16 mole) and diethyl ethoxymethylenemalonate (35 g., 0.17 mole) were combined and heated on a steam bath for 2 hours. 2-(2,2-dicarbethoxyethenylamino)-4-ethylthiazole was obtained as an oil on cooling, and was used directly in the next step. (Rf 0.75 on silica gel thin layer chromatography with chloroform/1% ethanol as eluant.)

By the same process, 2-amino-4-isopropylthiazole (58.6 g., 0.415 mole) and diethyl ethoxymethylenemalonate (92 ml., 0.455 mole) were converted to 2-(2,2-dicarbethoxyethenylamino)-4-isopropylthiazole. (Rf 0.7 on silica gel thin layer chromatography with chloroform/1% ethanol as eluant.)

EXAMPLE 24

2-(2,2-Dicarbethoxyethenylamino)-6-phenylcyclohexenothiazole

2-Amino-6-phenylcyclohexenothiazole (10.4 g., 45.2 mmole) and diethyl ethoxymethylenemalonate (10 ml., 49.5 mmole) were combined and heated on a steam bath. After 15 minutes, a solution resulted. After an additional 30 minutes of heating, the entire mass solidified. The crude product was recrystallized from cyclohexane to yield purified 2-(2,2-dicarbethoxyethenylamino)-6-phenylcyclohexenothiazole (15.3 g., m.p. 131°-133° C.).

EXAMPLE 25

2-(2,2-Dicarbethoxyethenylamino)-6-methylcyclohexenothiazole

2-Amino-6-methylcyclohexenothiazole (23.3 g., 0.139 mole) was combined with diethyl ethoxymethylenemalonate (31 ml., 0.153 mole) and heated on a steam bath. After about 10 minutes of heating, a clear orange oil resulted. After one hour of heating, crystallization was induced by scratching. Purified 2-(2,2-dicarbethoxyethenylamino)-6-methylcyclohexenothiazole (40.2 g., m.p. 106°-109° C.) was obtained by recrystallization from ethanol.

EXAMPLE 26

2-(2,2-Dicarbethoxyethenylamino)-6,6-dimethylcyclohexenothiazole

2-Amino-6,6-dimethylcyclohexenothiazole (9.8 g., 53.8 mmole), diethylethoxymethylenemalonate (12 ml., 59.4 mmole) and ethanol (approximately 5 ml.) were combined and heated on a steam bath for 1.5 hours. The ethanol boiled off during the early part of the heating period. Upon cooling and scratching the product crystallized. Purified 2-(2,2-dicarbethoxyethenylamino)-6,6-dimethylcyclohexenothiazole (14.3 g., m.p. 83°-85° C.) obtained by recrystallization from hexane.

Analysis Calcd.: $C_{17}H_{24}O_4N_2S$: C, 57.93; H, 6.86; N, 7.95.

Found: C, 57.72; H, 6.66; N, 7.94.

EXAMPLE 27

2-(2,2-Dicarbethoxyethenylamino)-4-(2-butyl)thiazole

2-Amino-4-(2-butyl)thiazole (8.44 g., 54 mmoles) and diethyl ethoxymethylenemalonate (11.7 g., 54 mmoles) were combined and heated on a steam bath for 1 hour and cooled to yield 2-(2,2-dicarbethoxyethenylamino)-4-(2-butyl)thiazole (17.6 g., Rf 0.75 on silica gel thin layer chromatography with chloroform/1% ethanol as eluant).

EXAMPLE 28

Ethyl 1-Oxo-1H-6,7-dimethylthiazolo[3,2-a]pyrimidine-2-carboxylate 2-(2-Dicarbethoxyethenylamino)-4,5-dimethylthiazole (4.17 g., 14 mmoles) was combined with 30 ml. of Dowtherm A and heated at 220° C. for 1.5 hours. The reaction mixture was cooled and about 125 ml. of petroleum ether added. The solid which separated was filtered off, recombined with mother liquor and chromatographed on a 70×180 mm. column of silica gel with chloroform as eluant. Following an initial fraction of 125 ml., six fractions of 250 ml. were collected, stripped to dryness to yield crude product (2.42 g., m.p. 114°-115° C.). Recrystallization from cyclohexane provided purified ethyl 1-oxo-1H-4,5-dimethylthiazolo[3,2-a]pyrimidine-2-carboxylate (1.64 g., m.p. 119°-120° C.).

Analysis Calcd.: $C_{11}H_{12}N_2O_3S$: C, 52.37; H, 4.79; N, 11.10; mass ion, 252;

Found: C, 52.21; H, 4.85; N, 11.23; mass ion, 252.

EXAMPLE 29

Ethyl 1-Oxo-1H-6-methyl-7-ethylthiazolo[3,2-a]pyrimidine-2-carboxylate 2-(2-Dicarbethoxyethenylamino)-4-ethyl-5-methylthiazole (6.25 g.) was combined with 30 ml. of Dowtherm A and heated to 215° C. for 2.5 hours. The reaction mixture was cooled, petroleum ether was added and the crude product (1.96 g.) recovered by filtration. Crude (630 mg.) was recrystallized from cyclohexane yielding purified 1-oxo-1H-6-methyl-7-ethylthizaolo[3,2-a]pyrimidine-2-carboxylate (301 mg., m.p. 122°-124° C.).

Analysis Calcd.: $C_{12}H_{14}N_2O_3S$: C, 54.12; H, 5.30; N, 10.52.

Found: C, 54.09; H, 5.26; N, 10.63.

EXAMPLE 30

Ethyl 1-Oxo-1H-6-ethyl-7-methylthiazolo[3,2-a]pyrimidine-2-carboxylate 2-(2,2-Dicarbethoxyethenylamino)-4-methyl-5-ethylthiazole (12 g.) was combined with 60 ml. of Dowtherm A and heated to 205° C. for 3 hours. The reaction mixture was cooled and chromatographed on a 90×205 mm. column of silica gel, eluting with chloroform containing 1% ethanol. Seven product-containing fractions of 250 ml. each were collected, combined, stripped to an oil and rechromatographed on silica gel (60×600 mm.) with the same eluant. Fractions (165×8 ml.) were combined, stripped to an oil and crystallized by trituration with diisopropyl ether. Recrystallization from cyclohexane yielded purified ethyl 1-oxo-1H-6-ethyl-7-methylthiazolo[3,2-a]pyrimidine-2-carboxylate (2.45 g., m.p. 65°-66° C.).

Analysis Calcd.: $C_{12}H_{14}N_2O_3S$: C, 54.12; H, 5.30; N, 10.52; mass ion, 266.

Found: C, 54.26; H, 5.23; N, 10.57; mass ion, 266.

EXAMPLE 31

Ethyl Oxo-1-1H-6,7-diethylthiazolo[3,2-a]pyrimidine-2-carboxylate

2(2,2-Dicarbethoxyethenylamino)-4,5-diethylthiazole (26.1 g.) and 300 ml. of Dowtherm A were combined and heated to 225° C. for 3.5 hours. The reaction mixture was cooled and chromatographed on a silica gel column (60×320 mm.). Dowtherm A was eluted with hexane and product was eluted with 2:1 hexane:-chloroform. Thirty-three fractions 250 ml. each were collected. The eighth to thirty-third were combined and stripped to yield ethyl 1-oxo-1H-6,7-diethyl-thiazolo[3,2-a]pyrimidine-2-carboxylate (22 g., Rf 0.4–0.5 on silica gel thin layer chromatography with chloroform-1% ethanol as eluant) as an oil.

By the same procedure, the following products are prepared from other compounds of examples 12 and 14:
2-(2,2-Dicarbomethoxyethenylamino)-4-ethyl-5-methylthiazole;
2-(2,2-Dicarbopropoxyethenylamino)-4-ethyl-5-methylthiazole;
2-(2,2-Dicarboisopropoxyethenylamino)-4-ethyl-5-methylthiazole;
2-(2,2-Dicarbomethoxyethenylamino)-4,5-diethyl-thiazole;
2-(2,2-Dicarbopropoxyethenylamino)-4,5-diethyl-thiazole;
2-(2,2-Dicarboisopropoxyethenylamino)-4,5-diethyl-thiazole;
2-(2,2-Dicarbethoxyethenylamino)-4-pentylthiazole;
2-(2,2-Dicarbethoxyethenylamino)-4-propyl-5-ethyl-thiazole;
2-(2,2-Dicarbethoxyethenylamino-4,5-diisopropyl-thiazole;
2-(2,2-Dicarbethoxyethenylamino)-5-propylthiazole;
2-(2,2-Dicarbethoxyethenylamino)-5-isopropylthiazole;
2-(2,2-Dicarbethoxyethenylamino)-5-pentylthiazole;
2-(2,2-Dicarbethoxyethenylamino)-6-phenylcyclopentenothiazole;
2-(2,2-Dicarbethoxyethenylamino)-5,7-dimethylcyclohexenothiazole
2-(2,2-Dicarbethoxyethenylamino)-7-methylcyclooctenothiazole and
2-(2,2-Dicarbethoxyethenylamino)-4,4,6-trimethylcyclopentenomethylthiazole are converted, respectively to:
Methyl 1-oxo-1H-6-methyl-7-ethylthiazolo[3,2-a]pyrimidine-2-carboxylate;
Propyl 1-oxo-1H-6-methyl-7-ethylthiazolo[3,2-a]pyrimidine-2-carboxylate;
Isopropyl 1-oxo-1H-6-methyl-7-ethylthiazolo[3,2-a]pyrimidine-2-carboxylate;
Methyl 1-oxo-1H-6,7-diethylthiazolo[3,2-a]pyrimidine-2-carboxylate;
Propyl 1-oxo-1H-6,7-diethylthiazolo[3,2-a]pyrimidine-2-carboxylate;
Isopropyl 1-oxo-1H-6,7-diethylthiazolo[3,2-a]pyrimidine-2-carboxylate;
Ethyl 1-oxo-1H-7-pentylthiazolo[3,2-a]pyrimidine-2-carboxylate;
Ethyl 1-oxo-1H-6-ethyl-7-propylthiazolo[3,2-a]pyrimidine-2-carboxylate;
Ethyl 1-oxo-1H-6,7-diisopropylthiazolo[3,2-a]pyrimidine-2-carboxylate;
Ethyl 1-oxo-1H-6-propylthiazolo[3,2-a]pyrimidine-2-carboxylate;
Ethyl 1-oxo-1H-6-isopropylthiazolo[3,2-a]pyrimidine-2-carboxylate;
Ethyl 1-oxo-1H-6-pentylthiazolo[3,2-a]pyrimidine-2-carboxylate;
Ethyl 1-oxo-1H-6-phenylcyclopentenothiazolo[3,2-a]pyrimidine-2-carboxylate;
Ethyl 1-oxo-1H-6,8-dimethylcyclohexenothiazolo[3,2-a]pyrimidine-2-carboxylate;
Ethyl 1-oxo-1H-8-methylcyclooctenothiazolo[3,2-a]pyrimidine-2-carboxylate and
Ethyl 1-oxo-1H-6,8,8-trimethylcyclopenteno-thiazolo[3,2-a]pyrimidine-2-carboxylate.

EXAMPLE 22

Ethyl 1-Oxo-1H-cyclopentenothiazolo[3,2-a]pyrimidine-2-carboxylate 2-(2,2-Dicarbethoxyethenylamino)cyclopenteno-thiazole (7.0 g.) was combined with 40 ml. of Dowtherm A and heated to 225°–230° C. for approximately 1 hour. The reaction was cooled and chromatographed on silica gel (70×190 ml.). Dowtherm A was eluted with hexane. Product was eluted with chloroform-1% ethanol. Four fractions of 250 ml. each were collected, combined and stripped of solvent to yield an oil. A portion of the oil was crystallized by triturated with cyclohexane to yield crude product (1.91 g.). Recrystallization of 0.6 g. of crude yielded purified ethyl 1-oxo-1H-cyclopentenothiazolo[3,2-a]pyrimidine-2-carboxylate (0.33 g., m.p. 102°–103° C.).

Analysis Calcd.: $C_{12}H_{12}N_2O_3S$: C, 54.53; H, 4.58; N, 10.60.

Found: C, 54.54; H, 4.71; N, 10.71.

EXAMPLE 33

Ethyl 1-Oxo-1H-cyclohexenothiazolo[3,2-a]pyrimidine-2-carboxylate 2-(2,2-Dicarbethoxyethenylamino)cyclohexeno-thiazole (12.6 g.) was combined with 125 ml. of Dowtherm A and heated at 230° C. for 25 minutes. The reaction mixture was cooled and chromatographed on silica gel (60×320 mm.). Dowtherm A was eluted with hexane and product eluted with chloroform-1% ethanol in 14 fractions of 125 ml. each. Crude ethyl 1-oxo-1H-cyclohexenothiazolo[3,2-a]pyrimidine-2-carboxylate (10.7 g., m.p. 92°–94° C.) was obtained by combining the fractions and stripping of solvent.

Alternatively, 2-(2,2-dicarbethoxyethenylamino)cyclohexenothiazole (80 g., 0.25 mole), trifluoroacetic anhydride (101 g., 68 ml., 0.48 mole), toluene (0.8 l.) and ethanol (1 l.) were combined and refluxed for 21 hours. The reaction mixture was cooled and 300 ml. of water added. The toluene (upper) layer was separated, washed with saturated aqueous sodium chloride, dried over anhydrous magnesium sulfate, filtered, concentrated to 150 ml. (slurry), diluted with 1 l. of ethanol (solution), concentrated to 280 ml., cooled to 5° C., granulated and filtered to yield relatively pure ethyl 1-oxo-1H-cyclohexenothiazolo[3,2-a]pyrimidine-2-carboxylate (47 g., m.p. 105°–106° C.).

EXAMPLE 34

Ethyl 1-Oxo-1H-cycloheptenothiazolo[3,2-a]pyrimidine-2-carboxylate

2-Aminocycloheptenothiazole (25.2 g., 0.15 mole), diethyl ethoxymethylenemalonate (35.7 g., 0.165 mole) and Dowtherm A (400 ml.) were combined and heated to 220°–230° C. for 2 hours. The reaction mixture was cooled and chromatographed on silica gel (90×235 mm.). Dowtherm A was eluted with hexane. Product was eluted with 1:1 hexane:chloroform in thirty fractions of 500 ml. each. The sixth to thirtieth fractions were combined and stripped to yield crude product as a wet solid. Purified ethyl 1-oxo-1H-cycloheptenothiazolo[3,2-a]pyrimidine-2-carboxylate (27.1 g., m.p. 78°–79° C.) was obtained by recrystallization from cyclohexane.

The same product is obtained by heating 2-(2,2-dicarbethoxyethenylamino)cycloheptenothiazole in Dowtherm A and isolating and purifying in a like manner.

EXAMPLE 35

Ethyl 1-Oxo-1H-cyclooctenothiazolo[3,2-a]pyrimidine-2-carboxylate 2-(2,2-Dicarbethoxyethenylamino)cyclooctenothiazole (3.13 g.) was combined with 30 ml. of Dowtherm A and heated to 220° C. for 2.5 hours. The reaction mixture was cooled and chromatographed on silica gel (70×190 mm.). Dowtherm A was eluted with hexane. The product was eluted with chloroform-1% ethanol in four 125 ml. fractions. The fractions were combined, stripped to an oil and solid ethyl 1-oxo-1H-cyclooctenothiazolo[3,2-a]pyrimidine-2-carboxylate (1.956 g., Rf. 0.5 on thin layer chromatography on silica gel eluted with chloroform-1% ethanol) obtained by trituration with hexane.

EXAMPLE 36

Ethyl 1-Oxo-1H-7-methylthiazolo[3,2-a]pyrimidine-2-carboxylate 2-(2,2-Dicarbethoxyethenylamino)-4-methylthiazole (9.8 g.) was combined with 50 ml. of Dowtherm A and heated to 220° C. for 2 hours. The reaction mixture was cooled and 50 ml. of hexane added and the crude product recovered by filtration. Recrystallization of the crude product from ethanol yielded purified ethyl 1-oxo-1H-7-methylthiazolo[3,2-a]pyrimidine-2-carboxylate (4.6 g., m.p. 187°–189° C.).

Alternatively, this ester is prepared by condensing 2-amino-4-methylthiazole directly with ethyl ethoxymethylenemalonate by refluxing in trichlorobenzene [Allen et. al., J. Org. Chem., 24, 779 (1959)].

EXAMPLE 37

Ethyl 1-Oxo-1H-thiazolo[3,2-a]pyrimidine-2-carboxylate 2-(2,2-Dicarbethoxyethenylamino)thiazole (17.2 g.) was combined with 200 ml. of Dowtherm A and heated to 215° C. for 30 minutes. The reaction mixture was cooled to yield a slurry. Hexane (100 ml.) was added and the crude product recovered by filtration. Recrystallization from ethanol yielded purified ethyl 1-oxo-1H-thiazolo[3,2-a]pyrimidine-2-carboxylate (8.0 g., m.p. 184°–185° C.).

Alternatively, this ester is prepared by condensing 2-aminothiazole directly with ethyl ethoxymethylenemalonate by refluxing in trichlorobenzene [Allen, et. al., J. Org. Chem., 24, 779 (1959)].

EXAMPLE 38

Ethyl 1-Oxo-1H-6-methylthiazolo[3,2-a]pyrimidine-2-carboxylate 2-(2,2-Dicarbethoxyethenyl)-5-methylthiazole (14.1 g.) was combined with 150 ml. of Dowtherm A and heated to 220° C. for 1.5 hours. The reaction mixture was cooled and about 300 ml. of hexane added. The product was recovered by filtration and purified ethyl 1-oxo-1H-6-methylthiazolo[3,2-a]pyrimidine-2-carboxylate (6.4 g., m.p. 149°–151° C.) obtained by recrystallization from diisopropyl ether.

Alternatively, this ester is prepared by condensing 2-amino-5-methylthiazole directly with ethyl ethoxymethylenemalonate in boiling trichlorobenzene (Dunwell, et. al., J. Chem. Soc., (C) 1971, 2094).

EXAMPLE 39

Ethyl 1-Oxo-1H-6-ethylthiazolo[3,2-a]pyrimidine-2-carboxylate 2-(2,2-Dicarbethoxyethenylamino)-5-ethylthiazole (25.7 g., 86 mmoles), trifluoroacetic anhydride (36.2 g., 172 mmoles) and toluene (150 ml.) were combined and heated to reflux for approximately 20 hours. The reaction mixture was stripped to dryness, taken up in 300 ml. of chloroform. The chloroform solution was washed with saturated sodium bicarbonate and then saturated sodium chloride, dried over anhydrous sodium sulfate, stripped to dryness and triturated with diisopropyl ether to yield ethyl 1-oxo-1H-6-ethylthiazolo[3,2-a]pyrimidine-2-carboxylate (17.8 g., m.p. 148°–150° C.). A portion of the product (5.2 g.) was recrystallized from approximately 75 ml. of ethyl acetate to yield further purified product (4.1 g., m.p. 149°–150° C.).

Analysis Calcd.: $C_{11}H_{12}N_2O_3S$: C, 52.37; H, 4.79; N, 11.10.

Found: C, 52.30; H, 4.51; N, 11.14.

EXAMPLE 40

Ethyl 1-Oxo-1H-7-(2-methyl-2-propyl)thiazolo[3,2-a]pyrimidine-2-carboxylate 2-(2,2-Dicarbethoxyethenylamino)-4-(2-methyl-2-propyl)thiazole (32.6 g.) was combined with 400 ml. of Dowtherm A and heated to 230° C. for 1 hour. The reaction mixture was cooled and chromatographed on silica gel (60×600 mm.). The Dowtherm A was eluted with hexane. The product was eluted with chloroform. Nine 500 ml. fractions were collected. The sixth through ninth fractions were combined and stripped to dryness yielding ethyl 1-oxo-1H-7-(2-methyl-2-propyl)thiazolo[3,2-a]pyrimidine-2-carboxylate (11.4 g., m.p. 145°–147° C.). Further product (2.04 g.) was obtained from the fifth fraction by stripping to a wet solid and triturating with cyclohexane. One gram of the larger crop was recrystallized from cyclohexane to yield further purified product (0.62 g., m.p. 148°–149° C.).

Analysis Calcd.: $C_{13}H_{16}N_2O_3S$: C, 55.70; H, 5.75; N, 9.99.

Found: C, 55.14; H, 5.58; N, 9.95.

EXAMPLE 41

Ethyl 1-Oxo-1H-7-ethylthiazolo[3,2-a]pyrimidine-2-carboxylate 2-(2,2-Dicarbethoxyethenylamino)-4-ethylthiazole (47.7 g., 0.16 mole) was stirred in 500 ml. of toluene and trifluoroacetic anhydride (45 ml., 0.32 mole) was added. A mild exotherm was noted. The reaction mixture was heated to reflux for 26 hours, cooled and 250 ml. of ethyl acetate added. The mixture was extracted cautiously with 250 ml. aqueous sodium bicarbonate (carbon dioxide evolution) and then with 250 ml. of saturated sodium chloride, dried over anhydrous sodium sulfate and stripped to dryness. The residue was slurried in diisopropyl ether and the crude product recovered by filtration. Recrystallization of the crude product from acetonitrile provided purified ethyl 1-oxo-1H-7-ethylthiazolo[3,2-a]pyrimidine-2-carboxylate (10.33 g., m.p. 175°–177° C.).

Analysis Calcd.: $C_{11}H_{12}N_2O_3S$: C, 52.37; H, 4.79; N, 11.10.

Found: C, 52.34; H, 4.85; N, 11.27.

A second crop (1.58 g., m.p. 176°–178° C.) was obtained from the acetonitrile mother liquor.

EXAMPLE 42

Ethyl 1-Oxo-4H-7-isopropylthiazolo[3,2-a]pyrimidine-2-carboxylate 2-(2,2-Dicarbethoxy)-4-isopropylthiazole (10 g.) was combined with 100 ml. of Dowtherm A and heated at 220° C. for 2 hours, cooled to room temperature overnight and reheated to 220° C. for an additional 5 hours. The mixture was cooled to room temperature, approximately 200 ml. of hexane was added and filtered to remove a trace of insolubles. The hexane was stripped and the residue chromatographed on approximately 500 g. of silica gel. The Dowtherm A was eluted with hexane and the product eluted with chloroform. Fractions containing product were combined and stripped to dryness, the residue slurried in diisopropyl ether and the product (m.p. 143°–144° C.) recovered by filtration. The crude was recrystallized from ethanol to yield purified ethyl 1-oxo-1H-7-isopropylthiazolo[3,2-a]pyrimidine-2-carboxylate (1.49 g., m.p. 145°–147° C., n.m.r.: singlets at $\delta 8.6$ and $\delta 7.3$ corresponding to one proton each, and multiplets centered at $\delta 4.2$ and $\delta 1.2$ corresponding to three protons and nine protons respectively).

EXAMPLE 43

Ethyl 1-Oxo-1H-7-phenylcyclohexenothiazolo[3,2-a]pyrimidine-2-carboxylate 2-(2,2-Dicarbethoxyethenylamino)-6-phenylcyclohexenothiazole (15.3 g., 38.2 mmoles) was slurried in 150 ml. of toluene. Trifluoroacetic anhydride (10.8 ml., 76.5 mmoles) was added, resulting in a clear solution which was refluxed for 16 hours. The reaction was cooled to room temperature, diluted with 150 ml. of ethyl acetate, extracted twice with 150 ml. of 5% potassium carbonate and once with 150 ml. of saturated sodium chloride, dried over anhydrous sodium sulfate and stripped to dryness. The solid residue was recrystallized from acetonitrile to yield purified ethyl 1-oxo-1H-7-phenylcyclohexenothiazole[3,2-a]pyrimidine-2-carboxylate (9.89 g., m.p. 160°–161.5° C.).

EXAMPLE 44

Ethyl 1-Oxo-1H-7-methylcyclohexenothiazolo[3,2-a]pyrimidine-2-carboxylate 2-(2,2-Dicarbethoxyethenylamino)-6-methylcyclohexenothiazole (40.2 g., 0.119 mole) was dissolved in 400 ml. of toluene. Trifluoroacetic anhydride (33.5 ml., 0.237 mole) was added, leading to a mild exotherm. The reaction mixture was refluxed overnight (16 hours), cooled to room temperature, diluted with 400 ml. of ethyl acetate, extracted twice with 400 ml. of 1 N potassium carbonate and once with 400 ml. of saturated sodium chloride, dried over anhydrous sodium sulfate and stripped to dryness. Recrystallization from cyclohexane containing a small amount of ethyl acetate provided purified ethyl 1-oxo-1H-7-methylcyclohexenothiazolo[3,2-a]pyrimidine-2-carboxylate (29.3 g., m.p. 127°–129° C.).

EXAMPLE 45

Ethyl 1-Oxo-1H-7,7-dimethylcyclohexenothiazolo[3,2-a]pyrimidine-2-carboxylate 2-(2,2-Dicarbethoxyethenylamino)-6,6-dimethylthiazole (13 g., 36.9 mmoles) was dissolved in 130 ml. of toluene. Trifluoroacetic anhydride (10.4 ml., 73.6 mmoles) was added and the mixture heated to reflux for 16 hours. The reaction was cooled to room temperature, diluted with 150 ml. of ethyl acetate, extracted twice with 130 ml. of saturated sodium bicarbonate and once with 150 ml. of saturated sodium chloride, dried over anhydrous sodium sulfate and stripped to dryness. Recrystallization from hexane provided purified ethyl 1-oxo-1H-7,7-dimethylcyclohexenothiazolo[3,2-a]pyrimidine-2-carboxylate (9.40 g., m.p. 92°–94° C.).

Analysis Calcd.: $C_{15}H_{16}N_2O_3S$: C, 58.80; H, 5.92, N, 9.14.

Found: C, 58.93; H, 5.48; N, 9.01.

EXAMPLE 46

Ethyl 1-Oxo-1H-7-(2-butyl)thiazolo[3,2-a]pyrimidine-2-carboxylate 2-(2,2-Dicarbethoxyethenylamino)-4-(2-butyl)-thiazole (17.6 g.) was combined with 175 ml. of Dowtherm A and heated to 225° C. for 2.5 hours. The reaction mixture was cooled and chromatographed on silica gel (60×600 mm.). Dowtherm A was eluted with hexane. Product was eluted with 2:1 chloroform:hexane. Fractions 4–8 (500 ml. each) were combined and stripped to an oil, which was taken up in approximately 400 ml. of hot hexane, treated with charcoal and cooled to yield crystalline ethyl 1-oxo-1H-7-(2-butyl)-thiazolo[3,2-a]pyrimidine-2-carboxylate (2.12 g., m.p. 105.5°–108° C.).

Analysis Calcd.: $C_{13}H_{16}O_3N_2S$: C, 55.70; H, 5.75; N, 9.99.

Found: C, 55.82; H, 5.40; N, 10.22.

EXAMPLE 47

1-Oxo-1H-6,7-dimethylthiazolo[3,2-a]pyrimidine-2-carboxylic Acid

Ethyl 1-oxo-1H-6,7-dimethylthiazolo[3,2-a]pyrimidine-2-carboxylate (1.41 g.) was heated on a steam bath with 20 ml. of 48% hydrobromic acid for 1 hour. Solution occurred within a few minutes and solids began to form at the end of the reaction period. The reaction mixture was cooled and the product recovered by filtration. Recrystallization from ethanol provided purified 1-oxo-1H-6,7-dimethylthiazolo[3,2-a]pyrimidine-2-carboxylic acid (508 mg., m.p. 189°–190° C.).

Analysis Calcd.: $C_9H_8O_3N_2S$: C, 48.21; H, 3.60; N, 12.49; mass ion, 224.

Found: C, 48.21; H, 3.68; N, 12.44; mass ion, 224.

EXAMPLE 48

1-Oxo-1H-6-methyl-7-ethylthiazolo[3,2-a]pyrimidine-2-carboxylic Acid

Ethyl 1-oxo-1H-6-methyl-7-ethylthiazolo[3,2-a]pyrimidine-2-carboxylate (971 mg.) was heated on a steam bath with 15 ml. of 48% hydrobromic acid. Dissolution occurred almost immediately. Heating was continued for 2.5 hours, at which time the reaction mixture was cooled, forming product as a filterable solid. Recrystallization of the crude product from isopropyl alcohol provided purified 1-oxo-1H-6-methyl-7-ethylthiazolo[3,2-a]pyrimidine-2-carboxylic acid (354 mg., m.p. 201°–202° C.).

Analysis Calcd.: $C_{10}H_{10}O_3N_2S$: C, 50.41; H, 4.23; N, 11.76.

Found: C, 50.28; L H, 4.26; N, 11.80.

EXAMPLE 49

1-Oxo-1H-6-ethyl-7-methylthiazolo[3,2-a]pyrimidine-2-carboxylic Acid

Ethyl 1-oxo-1H-6-ethyl-7-methylthiazolo[3,2-a]pyrimidine-2-carboxylate (1.33 g.) was heated on a steam bath with 10 ml. of 48% hydrobromic acid for 30 minutes, at which time a solid began to form. The mixture was cooled and crude product recovered by filtration. Recrystallization from isopropyl alcohol yielded purified 1-oxo-1H-6-ethyl-7-methylthiazolo[3,2-a]pyrimidine (596 mg., m.p. 174°–176° C.).

Analysis Calcd.: $C_{10}H_{10}O_3N_2S$: C, 50.41; H, 4.23; N, 11.76.

Found: C, 50.44; H, 4.22; N, 11.82.

EXAMPLE 50

1-Oxo-1H-6,7-diethylthiazolo[3,2-a]pyrimidine-2-carboxylic Acid

Ethyl 1-oxo-1H-6,7-diethylthiazolo[3,2-a]pyrimidine-2-carboxylate (19.2 g.) was heated to 85° C. with 48% aqueous HBr for 1 hour. Gassing (probable decarboxylation of product) was noted. The reaction mixture was cooled and rendered basic with conc. ammonium hydroxide and unreacted starting material and impurity extracted away with ethyl acetate. The aqueous phase was made acidic with acetic acid and solid product recovered by filtration. The crude was recrystallized from isopropyl alcohol, yielding partially purified product (5.4 g.) in two crops. Partially purified material (2.5 g.) was recrystallized a second time from isopropyl alcohol, yielding purified 1-oxo-1H-6,7-diethylthiazolo[3,2-a]pyrimidine-2-carboxylic acid [1.6 g., m.p. 104°–106° C. (cloudy)].

Analysis Calcd.: $C_{11}H_{12}O_3N_2S$: C, 52.37; H, 4.79; N, 11.10.

Found: C, 52.31; H, 4.79; N, 11.16.

EXAMPLE 51

1-Oxo-1H-cyclopentenothiazolo[3,2-a]pyrimidine-2-carboxylic Acid

Ethyl 1-oxo-1H-cyclopentenothiazolo[3,2-a]pyrimidine-2-carboxylate (1.3 g.) was heated with 15 ml. of 48% hydrobromic acid on a steam bath for 30 minutes. Dissolution occurred after about 5 minutes; a solid began to form by the end of the heating period. The reaction was cooled and crude product recovered by filtration. Recrystallization from isopropyl alcohol gave purified 1-oxo-1H-cyclopentenothiazolo[3,2-a]-pyrimidine (0.51 g., m.p. 202°–203.5° C.).

Analysis Calcd.: $C_{10}H_8O_3N_2S$: C, 50.84; H, 3.41; N, 11.86.

Found: C, 50.42; H, 3.57; N, 11.65.

The sodium and potassium salts are obtained by dissolving the free acid in water with one equivalent of the appropriate hydroxide and either stripping the water under vacuum or freeze drying.

The N-methylmorpholine salt is prepared by dissolving the acid in methylenechloride with a slight excess of N-methylmorpholine and stripping to dryness, or precipitating the salt by cooling and the addition of hexane.

EXAMPLE 52

1-Oxo-1H-cyclohexenothiazolo[3,2-a]-pyrimidine-2-carboxylic Acid

Ethyl-1-oxo-1H-cyclohexenothiazolo[3,2-a]pyrimidine-2-carboxylate (2.8 g.) was heated on a steam bath with 30 ml. of 48% hydrobromic acid. Solution occurred within a few minutes of the start of heating; precipitation of product had begun by the end of the reaction period. The reaction mixture was chilled in an ice bath and 1-oxo-1H-cyclohexenothiazolo[3,2-a]pyrimidine-2-carboxylic acid (1.66 g., m.p. 188°–189° C.) isolated by filtration. Recrystallization from ethanol gave 1.38 g. of the same melting point.

Alternatively, this product was prepared by stirring 22.3 g. of the ethyl ester with 223 ml. of 48% hydrobromic acid in a low pressure vessel. Solution occurred at 65°–70° C. The reaction mixture was warmed over a 40 minute period to a maximum temperature of 85° C. and a maximum pressure of 7 p.s.i.g. The reaction mixture was cooled to 45° C., vented, cooled to 5° C., stirred for 1 hour and the relatively pure product recovered directly by filtration (12.4 g., m.p.192°–194° C.).

The sodium salt is prepared by dissolving the acid in methanol with an equivalent of sodium methoxide and stripping to dryness or precipitating the salt by cooling and the addition of hexane.

EXAMPLE 53

1-Oxo-1H-cycloheptenothiazolo[3,2-a]pyrimidine-2-carboxylic Acid

Ethyl 1-oxo-1H-cycloheptenothiazolo[3,2-a]pyrimidine-2-carboxylate (5.8 g.) was heated for 15 minutes on a steam bath with 50 ml. of hydrobromic acid. The reaction was poured into ice, stirred and the crude product recovered by filtration. Recrystallization from ethanol gave purified 1-oxo-1H-cyclohepteno-thiazolo[3,2-a]pyrimidine (2.63 g., m.p. 162°–163° C.).

Analysis Calcd.: $C_{12}H_{12}O_3N_2S$: C, 54.53; H, 4.58; N, 10.60; mass ion, 264.

Found: C, 54.72; H, 4.73; N, 10.88; mass ion, 264.

Amine salts are prepared by addition of one equivalent of amine to a warm ethanol solution of the acid followed by cooling, concentration or the addition of hexane.

EXAMPLE 54

1-Oxo-1H-cyclooctenothiazolo[3,2-a]-pyrimidine-2-carboxylic Acid

Ethyl 1-oxo-1H-cyclooctenothiazolo[3,2-a]pyrimidine-2-carboxylate (1.23 g.) was heated in an oil bath with 30 ml. of 48% hydrobromic acid at 90° C. for 4 hours. The reaction mixture was cooled, the pH adjusted to 1.5 and the product extracted into ethyl acetate. The ethyl acetate extract was washed with water and then saturated sodium chloride, dried over sodium sulfate and stripped to an oil. The oil was redissolved in ethyl acetate and the product extracted into 1 N potassium hydroxide. The basic solution was reacidified with 3 N hydrochloric acid and the product extracted back into ethyl acetate. The ethyl acetate solution was extracted with water and then saturated sodium chloride, dried over anhydrous sodium sulfate and stripped to dryness to yield 1-oxo-1H-cycloheptenothiazolo[3,2-a]pyrimidine-2-carboxylic acid (308 mg., Rf 0.6 on silica gel thin layer chromatography with chloroform/1% ethanol as eluant).

The methodology of examples 47 to 53 is used to convert the corresponding alkyl 1-oxo-1H-thiazolo[3,2-a]pyrimidine-2-carboxylates of example 31 to:
1-Oxo-1H-6-methyl-7-ethylthiazolo[3,2-a]pyrimidine-2-carboxylic acid;
1-Oxo-1H-6,7-diethylthiazolo[3,2-a]pyrimidine-2-carboxylic acid;
1-Oxo-1H-7-pentylthiazolo[3,2-a]pyrimidine-2-carboxylic acid;
1-Oxo-1H-6-ethyl-7-propylthiazolo[3,2-a]pyrimidine-2-carboxylic acid;
1-Oxo-1H-6,7-diisopropylthiazolo[3,2-a]pyrimidine-2-carboxylic acid;
1-Oxo-1H-6-propylthiazolo[3,2-a]pyrimidine-2-carboxylic acid;
1-Oxo-1H-6-isopropylthiazolo[3,2-a]pyrimidine-2-carboxylic acid;
1-Oxo-1H-6-pentylthiazolo[3,2-a]pyrimidine-2-carboxylic acid;
1-Oxo-1H-6-phenylcyclopentenothiazolo[3,2-a]pyrimidine-2-carboxylic acid;
1-Oxo-1H-6,8-dimethylcyclohexenothiazolo[3,2-a]pyrimidine-2-carboxylic acid;
1-Oxo-1H-8-methylcyclooctenothiazolo[3,2-a]pyrimidine-2-carboxylic acid and
1-Oxo-1H-6,8,8-trimethylcyclopentenothiazolo[3,2-a]pyrimidine-2-carboxylic acid.

EXAMPLE 55

1-Oxo-1H-7-methylthiazolo[3,2-a]pyrimidine-2-carboxylic acid

Ethyl 1-oxo-1H-7-methylthiazolo[3,2-a]pyrimidine-2-carboxylate (3.1 g.) was heated on a steam bath with 50 ml. of 48% hydrobromic acid. Solution occurred within 5 minutes. After approximately 15 minutes of heating, the reaction mixture was cooled, and the product, which precipitated, recovered by filtration. Recrystallization from acetic acid gave purified 1-oxo-1H-7-methylthiazolo[3,2-a]pyrimidine-2-carboxylic acid [1.4 g; m.p. 265° C. (dec.)].

Analysis Calcd.: $C_8H_6O_3N_2S$: C, 45.71; H, 2.88; N, 13.33.

Found: C, 45.57; H, 3.04; N, 13.40.

EXAMPLE 56

1-Oxo-1H-thiazolo[3,2-a]-pyrimidine-2-carboxylic Acid

Ethyl 1-oxo-1H-thiazolo[3,2-a]pyrimidine-2-carboxylate (7.5 g.) was heated on a steam bath for 20 minutes with 80 ml. of 48% hydrobromic acid. Solution occurred within 5 minutes and precipitation of a solid began a few minutes later. The reaction was cooled in an ice bath and the crude product recovered by filtration. Recrystallization gave purified 1-oxo-1H-thiazolo[3,2-a]pyrimidine-2-carboxylic acid [4.66 g., m.p. 276° C. (dec.)].

Analysis Calcd.: $C_7H_4O_3H_2S$: C, 42.86; H, 2.06; N, 14.28.

Found: C, 42.71; H, 2.21; N, 14.32.

Alternatively, this acid may be prepared from the same intermediate by refluxing in excess 2 N hydrochloric acid [Allen et. al., J. Org. Chem., 24, 779 (1959)]

EXAMPLE 57

1-Oxo-1H-6-methylthiazolo[3,2-a]-pyrimidine-2-carboxylic Acid

Ethyl 1-oxo-1H-6-methylthiazolo[3,2-a]pyrimidine-2-carboxylate (5.96 g.) was heated on a steam bath for 1 hour with 60 ml. of 48% hydrobromic acid. The reaction was cooled in an ice bath and the crude product recovered by filtration, with isopropyl alcohol and ether washes. Recrystallization of the crude from dimethylformamide gave purified 1-oxo-1H-6-methylthiazolo[3,2-a]pyrimidine-2-carboxylic acid [3.73 g., m.p. 246°–248° C. (dec.)].

Analysis Calcd.: $C_8H_6O_3N_2S$: C, 45.71; H, 2.88; N, 13.33.

Found: C, 45.87; H, 2.94; N, 13.47.

Alternatively, this acid is prepared from the same intermediate by refluxing in 2 N hydrochloric acid (Dunwell et. al., J. Chem. Soc. (C) 1971, 2094).

EXAMPLE 58

1-Oxo-1H-6-ethylthiazolo[3,2-a]-pyrimidine-2-carboxylic Acid

Ethyl 1-oxo-1H-6-ethylthiazolo[3,2-a]pyrimidine-2-carboxylate (12.6 g.) was heated on a steam bath with 125 ml. of 48% hydrobromic acid. Dissolution occurred within a few minutes. After 10 minutes, a solid began to form. Heating was continued for a total of 40 minutes. The reaction mixture was cooled and the crude product (10.1 g.) recovered by filtration. Recrystallization of 2.32 g. crude product (of 6.8 g. recovered from attempted recrystallization from acetic acid) from isopropyl alcohol gave purified 1-oxo-1H-6-ethylthiazolo[3,2-a]pyrimidine-2-carboxylic acid (1.85 g., m.p. 162°–163° C.).

Analysis Calcd.: $C_9H_8O_3N_2S$: C, 48.21; H, 3.60; N, 12.49.

Found: C, 48.17; H, 3.73; N, 12.42.

EXAMPLE 59

1-Oxo-1H-7-(2-methyl-2-propyl(thiazolo[3,2-a]pyrimidine-2-carboxylic Acid

Ethyl 1-Oxo-1H-7-(2-methyl-2-propyl)thiazolo[3,2-a]-pyrimidine-2-carboxylate (5.6 g.) was heated on a steam bath for 6 hours with 60 ml. of 48% hydrobromic acid. After about 10 minutes, prior to complete solution of the ester, the reaction mixture became very thick. At the end of the heating period, the reaction mixture was cooled and crude product recovered by filtration. Recrystallization from acetic acid and drying over dimethylformamide gave purified 1-oxo-1H-7-(2-methyl-2-propyl)thiazolo[3,2-a]pyrimidine-2-carboxylic acid [3.33 g., m.p. 241°–242° C. (dec.)].

Analysis Calcd.: $C_{11}H_{12}O_3N_2S$: C, 52.37; H, 4.79; N, 11.10.

Found: C, 52.45; H, 4.82; N, 11.26.

EXAMPLE 60

1-Oxo-1H-7-ethylthiazolo[3,2-a]-pyrimidine-2-carboxylic Acid

Ethyl 1-oxo-1H-7-ethylthiazolo[3,2-a]pyrimidine-2-carboxylate (1.5 g.) was heated on a steam bath with 15 ml. of 48% hydrobromic acid for 20 minutes. Within 5 minutes, dissolution occurred and after 10 minutes, precipitation of a solid began. At the end of the reaction period, the mixture was cooled to room temperature, diluted with approximately 25 ml. of water and the crude product recovered by filtration. The crude product was partially purified by dissolution in 1 N potassium carbonate and reprecipitation by acidification with 3 N hydrochloric acid. Recrystallization from acetic acid gave purified 1-oxo-1H-7-ethylthiazolo[3,2-a]pyrimidine (594 mg., m.p. 206°–209° C.).

Analysis Calcd.: $C_9H_8N_2O_3S$: C, 48.21; H, 3.60; N, 12.49.

Found: C, 48.01; H, 3.69; N, 12.50.

EXAMPLE 61

1-Oxo-1H-7-isopropylthiazolo[3,2-a]-pyrimidine-2-carboxylic Acid

Ethyl 1-oxo-1H-7-isopropylthiazolo[3,2-a]pyrimidine-2-carboxylate (909 mg.) was heated on a steam bath with 10 ml. of 48% hydrobromic acid for 20 minutes. Within 5 minutes, complete dissolution occurred; within 10 minutes, product began to precipitate. After the heating period, the reaction mixture was cooled to room temperature and crude product recovered by filtration. Recrystallization from ethanol gave purified 1-oxo-1H-7-isopropylthiazolo[3,2-a]pyrimidine-2-carboxylic acid (538 mg., m.p. 216°–217° C.).

EXAMPLE 62

1-oxo-1H-7-phenylcyclohexenothiazolo[3,2-a]pyrimidine-2-carboxylic Acid

Ethyl 1-oxo-1H-7-phenylcyclohexenothiazolo[3,2-a]-pyrimidine-2-carboxylate (9.8 g.) was heated to reflux with 200 ml. of 48% hydrobromic acid for 20 minutes, solution occurring after about 10 minutes. The reaction mixture was cooled and the crude product recovered by filtration. Recrystallization from acetic acid gave purified 1-oxo-1H-7-phenylcyclohexenothiazolo[3,2-a]pyrimidine-2-carboxylic acid (2.25 g., m.p. 224°–226° C.).

Analysis Calcd.: $C_{17}H_{14}N_2O_3S$: C, 62.56; H, 4.32; N, 8.58.

Found: C, 62.6; H, 4.11; N, 8.52. A second crop was obtained from mother liquor. (704 mg., m.p. 217°–220° C.).

EXAMPLE 63

1-Oxo-1H-7-methylcyclohexenothiazolo[3,2-a]pyrimidine-2-carboxylic Acid

Ethyl 1-oxo-1H-7-methylcyclohexenothiazolo[3,2-a]pyrimidine-2-carboxylate (27.5 g.) was heated on a steam bath for 35 minutes with 275 ml. of 48% hydrobromic acid. After 10 minutes, clear solution resulted; after 15 minutes, precipitation of product began. The reaction mixture was cooled to room temperature and crude product (14.9 g., m.p. 181.5°–183.5° C.) recovered by filtration with water wash. Recrystallization from dimethylformamide gave purified 1-oxo-1H-7-methylcyclohexenothiazolo[3,2-a]pyrimidine-2-carboxylic acid (10.1 g., m.p. 183.5°–185.5° C.).

Analysis Calcd.: $C_{12}H_{12}N_2O_3S$: C, 54.53; H, 4.58; N, 10.60.

Found: C, 54.41; H, 4.28; N, 10.58.

A second crop was obtained by addition of water to the dimethylformamide mother liquor (3.11 g., m.p. 182°–184° C.).

EXAMPLE 64

1-Oxo-1H-7,7-dimethylcyclohexenothiazolo[3,2-a]pyrimidine-2-carboxylic Acid

Ethyl 1-oxo-1H-7,7-dimethylcyclohexenothiazolo[3,2-a]pyrimidine-2-carboxylate (7.9 g.) was combined with 80 ml. of 48% hydrobromic acid and heated on a steam bath for 50 minutes. Before dissolution of ester was complete, precipitation of acid began. The reaction mixture was cooled, diluted with about 100 ml. of water and crude product (6.7 g.) recovered by filtration, with a small volume of water wash. Recrystallization of the crude from ethanol gave purified 1-oxo-1H-7,7-dimethylcyclohexenothiazolo[3,2-a]pyrimidine-2-carboxylic acid (4.7 g., m.p. 197°–198° C.).

Analysis Calcd.: $C_{13}H_{14}N_2O_3S$: C, 56.10; H, 5.07; N, 10.06.

Found: C, 55.85; H, 4.84; N, 10.14.

EXAMPLE 65

1-Oxo-1H-7-(2-butyl)thiazolo[3,2-a]pyrimidine-2-carboxylic Acid

Ethyl 1-oxo-1H-7-(2-butyl)thiazolo[3,2-a]pyrimidine-2-carboxylate (2.0 g.) was combined with 20 ml. of 48% hydrobromic acid and heated on a steam bath for 25 minutes. Within 5 minutes, solution occurred; within 10 minutes, precipitation of product began. The reaction mixture was cooled to room temperature, diluted with approximately 40 ml. of water and crude product (1.3 g., m.p. 191°–194° C.) recovered by filtration with a small volume of water wash. Recrystallization of the crude from ethyl acetate containing a small amount of ethanol gave purified 1-oxo-1H-7-(2-butyl)thiazolo[3,2-a]-pyrimidine-2-carboxylic acid (606 mg., m.p. 194°–197° C.).

Analysis Calcd.: $C_{11}H_{12}N_2O_3S$: C, 52.37; H, 4.79; N, 11.10.

Found: C, 52.20; H, 4.48; N, 11.11.

The ethyl acetate mother liquor was concentrated to yield a small second crop.

EXAMPLE 66

N-(5-Tetrazolyl)-1-oxo-1H-6,7-dimethylthiazolo[3,2-a]pyrimidine-2-carboxamide

1-Oxo-1H-6,7-dimethylthiazolo[3,2-a]pyrimidine-2-carboxylic acid (367 mg., 1.6 mmoles) was dissolved in 3 ml. of dimethylformamide by heating on a steam bath. 1,1'-carbonyldiimidazole (292 mg., 1.8 mmoles) was added. There swas immediate evolution of a gas. As soon as gassing ceases, 5-aminotetrazole (153 mg., 1.8 mmoles) was added. Solution occurred, and a new solid formed. The reaction mixture was cooled and crude product recovered by filtration. Recrystallization of the crude from dimethylformamide gave purified N-(5-tetrazolyl)-1-oxo-1H-6,7-dimethylthiazolo[3,2-a]pyrimidine-2-carboxamide (336 mg., m.p. >317° C.).

Analysis Calcd.: $C_{10}H_9O_2N_7S$: C, 41.23; H, 3.11; N, 33.66.

Found: C, 41.52; H, 3.40; N, 33.47.

EXAMPLE 67

N-(5-Tetrazolyl)-1-oxo-1H-6-methyl-7-ethyl-thiazolo[3,2-a]pyrimidine-2-carboxamide 1-Oxo-1H-6-methyl-7-ethylthiazolo[3,2-a]pyrimidine-2-carboxylic acid (238 mg., 1.0 mmole) was dissolved in 5 ml. of dimethylformamide and heated on a steam bath. 1,1'-Carbonyldiimidazole (178 mg., 1.1 mmole) was added. When gassing ceased, 5-aminotetrazole (93.5 mg., 1.1 mmole) was added. A solid began to precipitate after approximately 15 minutes. The reaction mixture was cooled and filtered to yield N-(5-tetrazolyl)-1-oxo-1H-6-methyl-7-ethylthiazolo[3,2-a]pyrimidine-2-carboxamide (227 mg., m.p. >310° C.).

Analysis Calcd.: $C_{11}H_{11}O_2N_7S$: C, 43.27; H, 3.63; N, 32.11.

Found: C, 43.20; H, 3.72; N, 31.88.

EXAMPLE 68

N-(5-Tetrazolyl)-1-oxo-1H-6-ethyl-7-methyl-thiazolo[3,2-a]pyrimidine-2-carboxamide 1-Oxo-1H-6-ethyl-7-methylthiazolo[3,2-a]pyrimidine-2-carboxylic acid (476 mg., 2.0 mmoles) was dissolved in dimethylformamide on a steam bath. 1,1'-dicarbonyldiimidazole (357 mg., 2.2 mmoles) was added to the hot solution; gassing occurred. Once evolution of gas ceased, 5-aminotetrazole (187 mg., 2.2 mmoles) was added. Within a few minutes, a solid began to form. The reaction mixture was cooled and crude product recovered by filtration. Recrystallization from dimethylformamide gave purified N-(5-tetrazolyl)-1-oxo-1H-6-ethyl-7-methylthiazolo[3,2-a]pyrimidine-2-carboxamide [388 mg., m.p. 303° C. (dec.)].

Analysis Calcd.: $C_{11}H_{11}O_2N_7S$: C, 43.3; H, 3.6; N, 32.1.

Found: C, 43.6; H, 3.9; N, 32.3.

EXAMPLE 69

N-(5-Tetrazolyl)-1-oxo-1H-6,7-diethylthiazolo[3,2-a]pyrimidine-2-carboxamide

1-Oxo-1H-6,7-diethylthiazolo[3,2-a]pyrimidine-2-carboxylic acid (2.52 g., 10 mmoles) and 1,1'-carbonyldiimidazole (1.78 g., 11 mmoles) were combined with 15 ml. of dimethylformamide and heated on a steam bath. Gassing and solution occurred. When gassing ceased, 5-aminotetrazole (1.13 g., 11 mmoles) was added and heating continued for 30 minutes. The reaction mixture was cooled and the precipitated crude product recovered by filtration. Recrystallization of the crude product from acetic acid gave purified N-(5-tetrazolyl)-1-oxo-1H-6,7-diethylthiazolo[3,2-a]pyrimidine-2-carboxamide [1.11 g., m.p. 283° C. (dec.)].

Analysis Calcd.: $C_{12}H_{13}O_2N_7S$: C, 45.13; H, 4.10; N, 30.70; mass ion, 319.

Found: C, 45.18; H, 4.24; N, 30.52; mass ion, 319.

EXAMPLE 70

N-(5-Tetrazolyl)-1-oxo-1H-cyclopentenothiazolo[3,2-a]pyrimidine-2-carboxamide

1-Oxo-1H-cyclopentenothiazolo[3,2-a]pyrimidine-2-carboxylic acid (378 mg., 16 mmoles) and 1,1'-carbonyldiimidazole (285 mg., 17.6 mmoles) were combined with 3 ml. of dimethylformamide and heated on a steam bath; dissolution and gassing occurred. When gassing ceased, 5-aminotetrazole (150 mg., 17.6 mmoles) was added. Within a few minutes, product began to precipitate. The reaction mixture was cooled and crude product recovered by filtration. Recrystallization from dimethylformamide gave purified N-(5-tetrazolyl)-1-oxo-1H-cyclopentenothiazolo[3,2-a]pyrimidine-2-carboxamide (313 mg., m.p. >310° C.).

Analysis Calcd.: $C_{11}H_9O_2N_7S$: C, 43.6; H, 3.0; N, 32.3.

Found: C, 43.6; H, 3.3; N, 32.0.

EXAMPLE 71

N-(5-Tetrazolyl)-1-oxo-1H-cyclohexenothiazolo[3,2-a]pyrimidine-2-carboxamide

1-Oxo-1H-cyclohexenothiazolo[3,2-a]pyrimidine-2-carboxylic acid (0.5 g., 2 mmoles) and 1,1'-carbonyldiimidazole (0.36 g., 2.2 mmoles) were dissolved in 3 ml. of dimethylformamide at room temperature; solution and gassing occurred. When gassing ceased, the reaction was heated on a steam bath, during which time additional evolution of gas occurred. 5-Aminotetrazole (0.19 g., 2.2 mmoles) was added to the hot solution. Within a few minutes, precipitation of product commenced. The reaction mixture was cooled and crude product recovered by filtration. Recrystallization of the crude gave purified N-(5-tetrazolyl)-1-oxo-1H-cyclohexenothiazolo [3,2-a]pyrimidine-2-carboxamide [319 mg., m.p. 310° C. (dec.)].

Analysis Calcd.: $C_{12}H_{11}O_2N_7S$: C, 45.42; H, 3.49; N, 30.90.

Found: C, 45.59; H, 3.62; N, 30.44.

Alternatively, the acid (2.07 g.) was dissolved in 40 ml. of methylene chloride and 1.74 ml. of triethylamine at 0° C. Ethyl chloroformate (0.85 ml.) in 8.1 ml. of methylene chloride was added over 20 minutes, while maintaining the temperature of the reaction between 0° and 5° C. After holding at 0°-5° C. for 45 minutes, 5-aminotetrazole (0.87 g.) in 8.1 ml. of dimethylacetamide was added, and the reaction mixture was warmed to 20° C. over 25 minutes, and held at this temperature for 90 minutes. The product was recovered by filtration (2.0 g., m.p. 308°-310° C.). Product prepared in this manner (3.9 g.) was recrystallized from dimethylacetamide, yielding purified N-(5-tetrazolyl)-1-oxo-1H-cyclohexenothiazolo[3,2-a]pyrimidine-2-carboxamide (3.1 g., m.p. 314°-315° C.).

The sodium salt of this amide was prepared by dissolving 5.5 g., (17.3 mmoles) of the amide in 44 ml. of water and 17.3 ml. (17.3 mmoles) of standardized 1 N sodium hydroxide by stirring for 30 minutes (pH 11.0). The solution was clarified and the sodium salt precipitated by the addition of 35 ml. of acetone. The slurry was cooled to 5° C., granulated for 3 hours and the sodium salt (4.9 g.) recovered by filtration with cold acetone wash. This sodium salt (100 mg. slurried in 1 ml. of water) exhibited a pH of 10.22. The sodium salt was recrystallized by dissolution of 2.3 g. in 23 ml. of water at 60° C. The clear solution was cooled over 1 hour to 5° C. and granulated at this temperature for 1 hour. Sodium salt (1.68 g.) was recovered by filtration. The pH of 100 mg. of recrystallized sodium salt in 1 ml. of water was 8.80.

Analysis Calcd.: $C_{12}H_{10}O_2N_7SNa \cdot 3H_2O$: $H_2O$, 13.7; loss of weight on drying, 13.7; neutralization equiv., 393.

Found: $H_2O$, 13.43; loss of weight on drying, 13.8; neutralization equiv., 391.

In the mixed anhydride process described above, equivalent amounts of methyl chloroformate, propyl chloroformate, isopropyl chloroformate, butyl chloroformate, tert-butyl chloroformate, pentyl chloroformate, phenyl chloroformate or benzyl chloroformate are substituted for ethyl chloroformate with substantially similar results. Similarly, equivalent amounts of the other acids described in examples 47 to 65 are reacted with chloroformates, and thence with 5-aminotetrazole to yield the corresponding N-(5-tetrazolyl)amides.

EXAMPLE 72

N-(5-Tetrazolyl)-1-oxo-1H-cycloheptenothiazolo[3,2-a]pyrimidine-2-carboxamide

1-Oxo-1H-cyclopentenothiazolo[3,2-a]pyrimidine-2-carboxylic acid (2.1 g., 8 mmoles) and 1,1-carbonyldiimidazole (1.4 g., 8.8 mmoles) were combined with 15 ml. of dimethylformamide and heated on a steam bath. When gassing ceased, 5-aminotetrazole monohydrate (0.86 g., 8.8 mmoles) was added. A solid formed within 5 minutes. After an additional 30 minutes of heating, the reaction mixture was cooled and the product recovered by filtration. Recrystallization of crude product from dimethylformamide gave purified N-(5-tetrazolyl)-1-oxo-1H-cycloheptenothiazolo[3,2-a]pyrimidine-2-carboxamide [1.61 g., m.p. 295°–296° C. (dec.)].

Analysis Calcd.: $C_{13}H_{13}O_2N_7S$: C, 47.12; H, 3.95; N, 29.59.

Found: C, 47.10; H, 4.11; N, 29.72.

EXAMPLE 73

N-(5-Tetrazolyl)-1-oxo-1H-cyclooctenothiazolo[3,2-a]pyrimidine-2-carboxamide

1-Oxo-1H-cyclooctenothiazolo[3,2-a]pyrimidine-2-carboxylic acid (308 mg., 1.1 mmoles) was dissolved in 10 ml. of dimethylformamide and heated on a steam bath. 1,1'-Carbonylidiimidazole (196 mg., 1.21 mmoles) was added. When gassing ceased, 5-aminotetrazole (103 mg., 1.21 mmoles) was added. The reaction was heated for 10 minutes, during which a solid began to precipitate. The reaction was cooled and the crude product recovered by filtration. Recrystallization from dimethylformamide gave purified N-(5-tetrazolyl)-1-oxo-1H-cyloocetnothiazolo[3,2-a]pyrimidine-2-carboxamide [183 mg., m.p. 310° C. (dec.)].

Analysis Calcd.: $C_{14}H_{15}O_2N_7S$: C, 48.69; H, 4.38; N, 28.39.

Found: C, 49.01; H, 4.63; N, 27.35.

EXAMPLE 74

N-(5-Tetrazolyl)-1-oxo-1H-7-methylthiazolo[3,2-a]pyrimidine-2-carboxamide

1-Oxo-1H-7-methylthiazolo[3,2-a]pyrimidine-2-carboxylic acid (0.91 g., 4.3 mmoles) and 1,1'-carbonyldiimidazole (0.89 g., 5.5 mmoles) were placed in 5 ml. of dimethylformamide and heated on a steam bath. When gassing ceased, 5-aminotetrazole (0.47 g., 5.5 mmoles) was added. Before complete solution was achieved, a new solid began to precipitate. After a few minutes, the reaction was cooled and crude product recovered by filtration. Recrystallization from dimethylformamide gave purified N-(5-tetrazolyl)-1-oxo-1H-7-methylthiazolo[3,2-a]pyrimidine-2-carboxamide (1.0 g., m.p. >310° C.).

Analysis Calcd.: $C_9H_7O_2N_7S$: C, 38.99; H, 2.54; N, 35.36.

Found: C, 38.97; H, 2.73; N, 34.97.

EXAMPLE 75

N-(5-Tetrazolyl)-1-oxo-1H-thiazolo[3,2-a]pyrimidine-2-carboxamide 1-oxo-1H-thiazolo[3,2-a]pyrimidine-2-carboxylic acid (1.96 g., 10 mmoles) was dissolved in 20 ml. of dimethylformamide on a steam bath. 1,1'-carbonyldiimidazole (1.78 g., 11.0 mmoles) was added. When gassing ceased, 5-aminotetrazole monohydrate (1.13 g., 11 mmoles) was added. A solid formed in less than 1 minute. After heating for an additional 15 minutes, the reaction was cooled and crude product recovered by filtration. Recrystallization from dimethylformamide gave purified N-(5-tetrazolyl)-1-oxo-1H-thiazolo[3,2-a]pyrimidine-2-carboxamide (1.8 g., m.p. >315° C.).

Analysis Calcd.: $C_8H_5O_2N_7S$: C, 36.50; H, 1.91; N, 37.25.

Found: C, 36.62; H, 2.26; N, 37.72.

EXAMPLE 76

N-(5-Tetrazolyl)-1-oxo-1H-6-methylthiazolo[3,2-a]pyrimidine-2-carboxamide

1-Oxo-1H-6-methylthiazolo[3,2-a]pyrimidine-2-carboxylic acid (2.10 g., 10 mmoles) and 1,1'-carbonyldiimidazole (1.78 g., 11 mmoles) were combined with 15 ml. of dimethylformamide and heated on a steam bath. Gassing ensued and dissolution occurred. When gassing was complete, 5-aminotetrazole monohydrate (1.13 g., 11 mmoles) was added. A solid formed in less than a minute. After 5 minutes of heating, the reaction was cooled. Filtration gave N-(5-tetrazolyl)-1-oxo-1H-6-methylthiazolo[3,2-a]pyrimidine-2-carboxamide (2.33 g., m.p. >318° C.).

Analysis Calcd.: $C_9H_7O_2N_7S$: C, 38.99; H, 2.54; N, 35.36.

Found: C, 39.35; H, 3.00; N, 35.06.

EXAMPLE 77

N-(5-Tetrazolyl)-1-oxo-1H-6-ethylthiazolo[3,2-a]pyrimidine-2-carboxamide

1-Oxo-1H-6-ethylthiazolo[3,2-a]pyrimidine-2-carboxylic acid (4.48 g., 20 mmoles) and 1,1'-carbonyldiimidazole (3.57 g., 22 mmoles) were combind with 20 ml. of dimethylformamide and heated on a steam bath. Gassing and solution occurred. When gassing ceased, 5-aminotetrazole monohydrate (2.27 g., 22 mmoles) was added. Solid formed within 1 minute. The reaction was heated for an additional 15 minutes, cooled and the crude product recovered by filtration. Recrystallization from dimethylformamide gave purified N-(5-tetrazolyl)-1-oxo-1H-6-ethylthiazolo[3,2-a]pyrimidine-2-carboxamide [4.7 g., m.p. 274° C. (dec.)].

Analysis Calcd.: $C_{10}H_9O_2N_7S$: C, 41.23; H, 3.11; N, 33.66.

Found: C, 41.41; H, 3.30; N, 33.84.

EXAMPLE 78

N-(5-Tetrazolyl)-1-oxo-1H-7-(2-methyl-2-propyl)-thiazolo[3,2-a]pyrimidine-1-carboxamide 1-Oxo-1H-7-(2-methyl-2-propyl)thiazolo[3,2-a]pyrimidine-2-carboxylic acid (2.52 g., 10 mmoles) and 1,1'-carbonyldiimidazole (1.78 g., 11 mmoles) were combined with 15 ml. of dimethylformamide and heated on a steam bath. Gassing and solution occurred, and a solid formed within a few minutes. Heating was continued for a total of approximately 10 minutes. The reaction mixture was cooled and crude product recovered by filtration. Recrystallization from dimethylformamide gave purified N-(5-tetrazolyl)-1-oxo-1H-7-(2-methyl-2-propyl)thiazolo[3,2-a]pyrimidine-2-carboxamide [1.62 g., m.p. 280° C. (dec.)].

Analysis Calcd.: $C_{12}H_{13}O_2N_7S$: C, 45.13; H, 4.10; N, 30.70.

Found: C, 45.22; H, 4.40; N, 30.05.

EXAMPLE 79

N-(5-Tetrazolyl)-1-oxo-1H-7-ethylthiazolo[3,2-a]pyrimidine-2-carboxamide

1-Oxo-1H-7-ethylthiazolo[3,2-a]pyrimidine-2-carboxylic acid (502.5 mg., 2.24 mmoles) and 1,1'-carbonyldiimidazole (399.7 mg., 2.46 mmoles) were combined with 3 ml. of dimethylformamide and heated on a steam bath. Solution and gassing resulted. After gassing ceased, 5-aminotetrazole monohydrate (253.0 mg., 2.45 mmoles) was added. A clear solution resulted; after 2 minutes, a solid began to precipitate. The mixture was heated for an additional 20 minutes, cooled to room temperature and crude product recovered by filtration. Recrystallization from dimethylformamide gave purified N-(5-tetrazolyl)-1-oxo-1H-7-ethylthiazolo[3,2-a]pyrimidine-2-carboxamide [486.8 mg; m.p. 261°-262° C. (dec.)].

Analysis Calcd.: $C_{10}H_9N_7O_2S$: C, 41.23; H, 3.11, N, 33.66; mass ion, 291.

Found: C, 41.35; H, 3.31; N, 33.35; mass ion, 291.

EXAMPLE 80

N-(5-Tetrazolyl)-1-oxo-1H-7-isopropylthiazolo[3,2-a]pyrimidine-2-carboxamide

1-Oxo-1H-7-isopropylthiazolo[3,2-a]pyrimidine-2-carboxylic acid (537 mg., 2.25 mmoles) and 1,1'-carbonyldiimidazole (401 mg., 2.47 mmoles) were combined with 3 ml. of dimethylformamide and heated on a steam bath. Dissolution and gassing occurred. After gassing ceased, 5-aminotetrazole monohydrate (255 mg., 2.47 mmoles) was added. Precipitation of product began immediately. Heating was continued for 20 minutes, after which the reaction was cooled and crude product recovered by filtration. Recrystallization from dimethylformamide gave purified N-(5-tetrazolyl)-1-oxo-1H-7-isopropylthiazolo[3,2-a]pyrimidine-2-carboxamide (328 mg., m.p. >300° C.).

Analysis Calcd.: $C_{11}H_{11}O_2N_7S$: C, 43.27; H, 3.63; N, 32.11.

Found: C, 43.34; H, 3.76; H, 31.82.

EXAMPLE 81

N-(5-Tetrazolyl)-1-oxo-1H-7-phenylcyclohexenothiazolo[3,2-a]pyrimidine-2-carboxamide 1-Oxo-1H-7-phenylcyclohexenothiazolo[3,2-a]pyrimidine-2-carboxylic acid (980 mg., 3.0 mmoles) and 1,1'-carbonyldiimidazole (320 mg., 3.1 mmoles) were combined with 12 ml. of dimethylformamide and the mixture heated on a steam bath. When gassing ceased, 5-aminotetrazole monohydrate (496 mg., 3.1 mmoles) was added. After 10 minutes, product began to precipitate. After a total of 1 hour of heating, the reaction was cooled to room temperature and the crude product (312 mg.) recovered by filtration. Recrystallization from dimethylformamide gave purified N-(5-tetrazolyl)-1-oxo-1H-7-phenylcyclohexenothiazolo[3,2-a]pyrimidine-2-carboxamide (131.5 mg., m.p. >300° C.).

Analysis Calcd.: $C_{18}H_{15}O_2N_7S$: C, 54.95; H, 3.84; N, 24.92.

Found: C, 54.38; H, 3.93; N, 24.61.

EXAMPLE 82

N-(5-Tetrazolyl)-1-oxo-1H-7-methylcyclohexenothiazolo[3,2-a]pyrimidine-2-carboxamide 1-Oxo-1H-7-methylcyclohexenothiazolo[3,2-a]pyrimidine-2-carboxylic acid (1.0 g., 3.78 mmoles) and 1,1'-carbonyldiimidazole (675 mg., 4.16 mmoles) were combined in 6 ml. of dimethylformamide and heated on a steam bath. Gas was evolved and a solution resulted. After gas evolution had stopped, 5-aminotetrazole (429 mg., 4.16 mmoles) was added and heating continued. After a few minutes, a precipitate began to form. After 30 minutes, the reaction was cooled and crude product (m.p. >300° C.) recovered by filtration. Recrystallization from dimethylformamide gave purified N-(5-tetrazolyl)-1-oxo-1H-7-methylcyclohexenothiazolo[3,2-a]pyrimidine-2-carboxamide (980 mg., m.p. >300° C.).

Analysis Calcd.: $C_{13}H_{13}O_2N_7S$: C, 47.12; H, 3.95; N, 29.59.

Found: C, 47.32; H, 4.18; N, 29.60.

EXAMPLE 83

N-(5-Tetrazolyl)-1-oxo-1H-7,7-dimethylcyclohexenothiazolo[3,2-a]pyrimidine-2-carboxamide 1-Oxo-1H-7,7-dimethycyclohexenothiazolo[3,2-a]pyrimidine-2-carboxylic acid (558 mg., 2.0 mmoles) and 1,1'-carbonyldiimidazole (357 mg., 2.2 mmoles) were combined with 3 ml. of dimethylformamide and heated on a steam bath; gassing ensued and a solution resulted. Once gas evolution ceased, 5-aminotetrazole monohydrate (227 mg., 2.2 mmoles) was added and heating continued for 20 minutes. The reaction was cooled and the crude product (561 mg., m.p. >300° C.) recovered by filtration. Recrystallization from dimethylformamide gave purified N-(5-tetrazolyl)-1-oxo-1H-7,7-dimethylthiazolo[3,2-a]pyrimidine-2-carboxamide (469 mg., m.p. >300° C.).

Analysis Calcd.: $C_{14}H_{15}O_2N_7S$: C, 48.69; H, 4.38; N, 28.39.

Found: C, 48.80; H, 4.18; N, 28.42.

EXAMPLE 84

N-(5-Tetrazolyl)-1-oxo-1H-7-(2-butyl)thiazolo[3,2-a]pyrimidine-2-carboxamide

1-Oxo-1H-7-(2-butyl)thiazolo[3,2-a]pyrimidine-2-carboxylic acid (379 mg., 1.5 mmoles) and 1,1'-carbonyldiimidazole (270 mg., 1.66 mmoles) were combined in 3 ml. of dimethylformamide and heated on a steam bath. Gas was evolved and a solution resulted. After gassing was complete, 5-aminotetrazole monohydrate (170 mg., 1.65 mmoles) was added and the mixture, which began to form a precipitate after a few minutes, heated for 20 minutes. The reaction was cooled to room temperature crude product recovered by filtration. Recrystallization gave purified N-(5-tetrazolyl)-1-oxo-1H-7-(2-butyl)-thiazolo[3,2-a]pyrimidine (247 mg., m.p. >300° C.).

Analysis Calcd.: $C_{12}H_{13}O_2N_7S$: C, 45.13; H, 4.10; N, 30.70.

Found: C, 45.12; H, 4.05; N, 30.68.

EXAMPLE 85

Following the methodology of examples 66 to 84, the following compounds are prepared from the corresponding 1-oxo-1H-thiazolo[3,2-a]pyrimidine-2-carboxylic acids:

N-(5-Tetrazolyl)-1-oxo-1H-7-pentylthiazolo[3,2-a]pyrimidine-2-carboxamide;

N-(5-tetrazolyl)-1-oxo-1H-6-ethyl-7-propylthiazolo[3,2-a]-pyrimidine-2-carboxamide;

N-(5-tetrazolyl)-1-oxo-1H-6,7-diisopropylthiazolo[3,2-a]-pyrimidine-2-carboxamide;

N-(5-tetrazolyl)-1-oxo-1H-6-propylthiazolo[3,2-a]pyrimidine-2-carboxamide;

N-(5-tetrazolyl)-1-oxo-1H-6-isopropylthiazolo[3,2-a]-pyrimidine-2-carboxamide;

N-(5-tetrazolyl)-1-oxo-1H-6-pentylthiazolo[3,2-a]pyrimidine-2-carboxamide;

N-(5-tetrazolyl)-1-oxo-1H-6-phenylcyclopentenothiazolo[3,2-a]pyrimidine-2-carboxamide;

N-(5-tetrazolyl)-1-oxo-1H-6,8-dimethylcyclohexenothiazolo[3,2-a]pyrimidine-2-carboxamide N-(5-tetrazolyl)-1-oxo-1H-8-methylcycloocteno-thiazolo[3,2-a]pyrimidine-2-carboxamide and N-(5-tetrazolyl)-1-oxo-1H-6,8,8-trimethylcyclopentenomethylthiazolo[3,2-a]pyrimidine-2-carboxamide.

EXAMPLE 86

Capsules

Capsules are prepared by blending the following ingredients in the proportion by weight indicated:

| | |
|---|---|
| Calcuim carbonate, U.S.P. | 17.6 |
| Dicalcium phosphate | 18.8 |
| Magnesium trisilicate, U.S.P. | 5.2 |
| Lactose, U.S.P. | 5.2 |
| Potato starch | 5.2 |
| Magnesium stearate A | 0.8 |
| Magnesium stearate B | 0.35 | and adding sufficient sodium N-(5-tetrazolyl)-1-oxo-1H-cyclohexenothiazolo[3,2-a]pyrimidine-2-carboxamide trihydrate to provide capsules containing 10, 25 and 50 mg. of active ingredient (weights equivalent to the nonsolvated, non-salt form) per capsule. The compositions can be filled into conventional hard gelatin capsules in the amount of 350 mg. per capsule.

In like manner, capsules containing 2.0 mg. and 6.0 mg. of active ingredient, and having 300 mg. of the following blends per capsule are prepared:

| Ingredients | Weight mg./capsule |
|---|---|
| Drug | 2.00 |
| N—methylglucamine | 18.00 |
| Lactose, anhydrous | 251.20 |
| Corn starch, anhydrous | 8.80 |
| Drug | 6.00 |
| N—methylglucamine | 18.00 |
| Lactose, anhydrous | 237.20 |
| Corn starch, anhydrous | 30.00 |
| Talc | 8.80 |

EXAMPLE 87

Tablets

A tablet base is prepared by blending the following ingredients in the proportion by weight indicated:

| | |
|---|---|
| Sucrose, U.S.P. | 80.3 |
| Tapioca Starch | 13.2 |
| Magnesium Stearate | 6.5 |

Into this tablet base sufficient sodium N-(5-tetrazolyl)-1-oxo-1H-cyclohexenothiazolo[3,2-a]pyrimidine-2-carboxamide trihydrate is blended to provide tablets containing 20, 100, and 250 mg. of active ingredient per tablet. The compositions are each compressed into tablets by conventional means. For tablets of lower potency, (e.g. 1 mg., 2 mg., 5 mg.) a lower ratio of active to inert ingredients is employed in the tablet base.

EXAMPLE 88

Solution

A solution of sodium N-(5-tetrazolyl)-1-oxo-1H-cyclohexenothiazolo[3,2-a]pyrimidine-2-carboxamide is prepared as follows:

| | |
|---|---|
| Active ingredient: | 6.04 g. (7.49 g. of sodium salt, trihydrate) |
| Magnesium chloride hexahydrate: | 12.36 g. |
| Propylene glycol: | 376.00 g. |
| Water, distilled: | 103 ml. |

The resultant solution has a concentration of effective ingredient of 10 mg./ml. and is suitable for parenteral and, especially, for intramuscular administration.

EXAMPLE 89

Aerosol Suspension

For use specifically as an antiallergy agent, a mixture of sodium N-(5-tetrazolyl)-1-oxo-1H-cyclohexenothiazolo[3,2-a]pyrimidine-2-carboxamide and the other ingredients under (a) in the tables immediately below are micronized to a particle size of 1 to 5 microns in a ball mill. The resulting slurry is then placed in a container equipped with a valve and propellant (b) introduced by pressure filling through the valve nozzle to a gauge pressure of approximately 35–40 pounds per square inch at 20° C.

|  | Percent |
| --- | --- |
| Suspension A | |
| (a) Antiallergy agent (equiv. to non-solvated, non-salt) | 0.25 |
| Isopropyl myristate | 0.10 |
| Ethanol | 26.40 |
| (b) 60–40% mixture of 1,2-dichlorotetra-flouroethane-1-chloropentafluoroethane | 73.25 |
| Suspension B | |
| (a) Antiallergy agent (equiv. to non-solvate, non-salt) | 0.25 |
| Ethanol | 26.52 |
| (b) 60–40% mixture of 1,2-dichlorotetra-fluoroethane-1-chloropentafluoroethane | 73.25 |
| Suspension C | |
| (a) Antiallergy agent (equiv. to non-solvated, non-salt) | 2.00 |
| Ethanol | 26.50 |
| (b) 60–40% mixture of 1,2-dichlorotetra-fluoroethane-1-chloropentafluoroethane | 71.50 |

I claim:

1. A compound of the formula

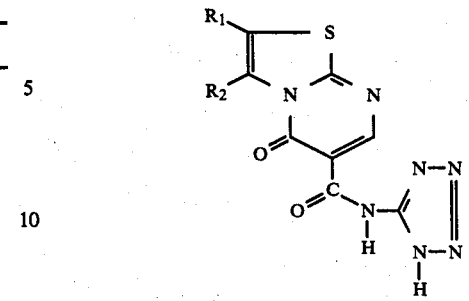

and pharmaceutically-acceptable cationic salts thereof, wherein $R_1$ and $R_2$ taken together are alkylene of 3 to 9 carbon atoms or phenylalkylene of 9 to 11 carbon atoms, with the proviso that the ring system so formed is 5- to 8-membered and $R_1$ and $R_2$ taken separately are each hydrogen or alkyl of 1 to 5 carbon atoms.

2. A compound of claim 1, wherein $R_1$ and $R_2$ are taken together and are alkylene of 3 to 6 carbon atoms.

3. A compound of claim 2, wherein $R_1$ and $R_2$ are taken together and are butylene.

4. The compound of claim 3, wherein the pharmaceutically-acceptable cationic salt is sodium.

5. A compound of claim 1, wherein $R_1$ is hydrogen or methyl and $R_2$ is methyl.

6. A compound of claim 5, wherein $R_1$ is hydrogen.

7. A compound of claim 1 wherein $R_1$ and $R_2$ are taken separately and $R_2$ is hydrogen.

8. The compound of claim 7 wherein $R_1$ is methyl.

9. The compound of claim 7 wherein $R_2$ is ethyl.

* * * * *